(12) United States Patent
Schofield et al.

(10) Patent No.: US 12,290,304 B2
(45) Date of Patent: May 6, 2025

(54) ELECTROSURGICAL CONNECTION UNIT

(71) Applicant: CMR SURGICAL LIMITED, Cambridge (GB)

(72) Inventors: Simon Schofield, Cambridge (GB); Paul Christopher Roberts, Cambridge (GB); Gordon Thomas Deane, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 0 days.

(21) Appl. No.: 18/389,886

(22) Filed: Dec. 20, 2023

(65) Prior Publication Data

US 2024/0115311 A1 Apr. 11, 2024

Related U.S. Application Data

(63) Continuation of application No. 16/289,854, filed on Mar. 1, 2019, now Pat. No. 11,882,989.

(30) Foreign Application Priority Data

Mar. 1, 2018 (GB) ...................................... 1803379

(51) Int. Cl.
*A61B 18/14* (2006.01)
*A61B 18/00* (2006.01)
(Continued)

(52) U.S. Cl.
CPC ...... *A61B 18/1482* (2013.01); *A61B 18/1206* (2013.01); *A61B 18/1233* (2013.01);
(Continued)

(58) Field of Classification Search
CPC ...... A61B 18/1482; A61B 2018/00178; A61B 2018/00773; A61B 34/30; A61B 2034/302
See application file for complete search history.

(56) References Cited

U.S. PATENT DOCUMENTS 5,067,953 A 11/1991 Feucht
5,626,575 A 5/1997 Crenner
(Continued)

FOREIGN PATENT DOCUMENTS

CN 103118614 A 5/2013
CN 104582629 A 4/2015
(Continued)

*Primary Examiner* — Joseph A Stoklosa
*Assistant Examiner* — Annie L Shoulders
(74) *Attorney, Agent, or Firm* — Occhiuti & Rohlicek LLP

(57) ABSTRACT

An electrosurgical connection unit for a surgical robot arm to connect an electrosurgical instrument attached to the arm to an electrosurgical generator. The electrosurgical connection unit includes an input port connectable to the electrosurgical generator, the input port configured to receive a driving electrosurgical signal and output one or more activation signals; an output port connectable to the electrosurgical instrument, the output port configured to output the driving electrosurgical signal received on the input port; one or more activation switch units, wherein activation of an activation switch unit causes an activation signal to be output from the input port indicating a driving electrosurgical signal with a desired waveform is to be activated; and a control unit configured to selectively activate one of the one or more activation switch units in response to a control signal.

20 Claims, 14 Drawing Sheets

(51) Int. Cl.
  *A61B 18/12* (2006.01)
  *A61B 34/30* (2016.01)
  *A61B 17/00* (2006.01)
(52) U.S. Cl.
  CPC .............. *A61B 18/14* (2013.01); *A61B 34/30* (2016.02); *A61B 2017/00141* (2013.01); *A61B 2017/00154* (2013.01); *A61B 2018/00083* (2013.01); *A61B 2018/00178* (2013.01); *A61B 2018/00589* (2013.01); *A61B 2018/00601* (2013.01); *A61B 2018/00607* (2013.01); *A61B 2018/00773* (2013.01); *A61B 2018/00875* (2013.01); *A61B 2018/00886* (2013.01); *A61B 2018/00928* (2013.01); *A61B 2018/00958* (2013.01); *A61B 2034/302* (2016.02); *A61B 2034/306* (2016.02)

(56) References Cited

U.S. PATENT DOCUMENTS

| | | | |
|---|---|---|---|
| 11,882,989 B2* | 1/2024 | Schofield | A61B 18/14 |
| 2004/0133189 A1 | 7/2004 | Sakurai | |
| 2004/0186376 A1 | 9/2004 | Hogg et al. | |
| 2007/0167720 A1* | 7/2007 | Viswanathan | A61B 34/73 |
| | | | 600/407 |
| 2011/0028969 A1 | 2/2011 | Sartor | |
| 2012/0330307 A1* | 12/2012 | Ladtkow | A61B 18/1482 |
| | | | 606/42 |
| 2013/0217967 A1 | 8/2013 | Mohr et al. | |
| 2013/0274729 A1* | 10/2013 | Orszulak | A61B 18/1445 |
| | | | 606/33 |
| 2014/0018795 A1 | 1/2014 | Shilev et al. | |
| 2014/0068770 A1 | 3/2014 | Chizeck et al. | |
| 2014/0246477 A1* | 9/2014 | Koch, Jr. | A61B 90/90 |
| | | | 227/180.1 |
| 2016/0203282 A1 | 7/2016 | Azizian et al. | |
| 2016/0314711 A1 | 10/2016 | Grubbs | |
| 2016/0338760 A1 | 11/2016 | Houser et al. | |
| 2017/0086908 A1* | 3/2017 | Wiener | A61B 18/1445 |
| 2019/0083190 A1* | 3/2019 | Graves | A61B 34/37 |
| 2019/0277912 A1 | 9/2019 | Panesar | |

FOREIGN PATENT DOCUMENTS

| | | |
|---|---|---|
| CN | 104815399 A | 8/2015 |
| CN | 105208956 A | 12/2015 |
| EP | 0423757 A1 | 4/1991 |
| GB | 2266817 A | 11/1993 |
| JP | 03-004846 A | 1/1991 |
| JP | 2016506841 A | 3/2016 |
| JP | 2016512051 A | 4/2016 |
| KR | 101447931 B1 | 10/2014 |
| WO | 2009105488 A2 | 8/2009 |
| WO | 2013/154924 A1 | 10/2013 |
| WO | 2015/132549 A1 | 9/2015 |
| WO | 2017/058617 A2 | 4/2017 |

* cited by examiner

ELECTROSURGICAL CONNECTION UNIT

CROSS-REFERENCE TO RELATED APPLICATIONS

This application is a continuation of U.S. application Ser. No. 16/289,854, filed Mar. 1, 2019, which claims priority to and the benefit of the filing date of UK Application No. GB 1803379.5, filed Mar. 1, 2018, the contents of all of which are hereby incorporated by reference in their entireties.

BACKGROUND

It is known to use robots for assisting and performing surgery. FIG. 1 illustrates a typical surgical robot 100 which comprises a base 108, an arm 102, and an instrument 105. The base supports the robot, and is itself attached rigidly to, for example, the operating theatre floor, the operating theatre ceiling or a trolley. The arm extends between the base and the instrument. The arm is articulated by means of multiple flexible joints 103 along its length, which are used to locate the surgical instrument in a desired location relative to the patient. The surgical instrument is attached to the distal end 104 of the robot arm. The surgical instrument penetrates the body of the patient 101 at a port 107 so as to access the surgical site. At its distal end, the instrument comprises an end effector 106 for engaging in a medical procedure.

A variety of surgical instruments are known, each adapted to perform a particular surgical function. FIG. 2 illustrates an example surgical instrument 200. The surgical instrument comprises a base 201 by means of which the surgical instrument connects to the robot arm. A shaft 202 extends between the base 201 and an articulation 203. The articulation 203 terminates in an end effector 204. The articulation 203 permits the end effector 204 to move relative to the shaft 202. It is desirable for at least two degrees of freedom to be provided to the motion of the end effector 204 by means of the articulation.

An electrosurgical instrument is a surgical instrument adapted to perform electrosurgery. As is known to those of skill in the art, electrosurgery is the passing of a high frequency (i.e. radio frequency) current through tissue to cause a desired effect (e.g. cutting the tissue or coagulating the tissue). Although the term electrosurgery is often used interchangeably with the term electrocautery, electrosurgery and electrocautery are separate and distinct procedures. Where electrocautery uses heat conduction from a probe heated by a direct current (DC), electrosurgery uses radio frequency (RF) alternating current (AC) to heat the tissue by RF induced intracellular oscillation of ionized molecules that result in an intracellular temperature. Accordingly, during electrosurgery the patient is included in the circuit and current enters the patient's body, whereas during electrocautery current does enter the patient's body.

There are two types of electrosurgery—monopolar and bipolar. In monopolar electrosurgery the high frequency current passes through the patient from a live or active electrode of the electrosurgical instrument to a separate return electrode placed on the patient, which may also be referred to as a dispersive electrode pad, a grounding pad, a neutral electrode, a grounding mat, an indifferent electrode or a patient electrode. In bipolar electrosurgery the active and return electrodes are both within the electrosurgical instrument and the current passes through the patient from the active electrode of the electrosurgical instrument to the return electrode of the electrosurgical instrument. An electrosurgical instrument which is configured for monopolar electrosurgery (e.g. an electrosurgical instrument that comprises an active electrode only) will be referred to herein as a monopolar electrosurgical instrument, and an electrosurgical instrument which is configured for bipolar electrosurgery (e.g. an electrosurgical instrument that comprises both an active electrode and a return electrode) will be referred to herein as a bipolar electrosurgical instrument.

Electrosurgical instruments receive the high frequency current (which is referred to herein as a driving electrosurgical signal) from an electrosurgical generator, which may also be referred to as an electrosurgery generator, electrosurgical end unit, electrosurgery end unit, or ESU. Electrosurgical generators are generally capable of generating multiple different current waveforms to achieve different surgical effects. For example, many standard electrosurgical generators can be configured to generate COAG, CUT and BLEND waveforms. The COAG waveform consists of bursts of radio frequency, which when used at a low power setting causes a desiccation effect, and when used at a high-power setting causes a fulguration effect. The CUT waveform is a continuous waveform at lower voltage, but higher current than COAG, which causes the tissue to be cut. A BLEND waveform is essentially a CUT waveform with a lower duty cycle than a CUT waveform. A BLEND waveform typically has a duty cycle between 15% to 75% whereas a CUT waveform typically has a duty cycle greater than 75%. The off time allows the tissue to cool creating some haemostasis. Accordingly, a BLEND waveform is used where haemostasis is required as tissue is cut. It will be evident to a person of skill in the art that these are examples only and that different electrosurgical generators may be configured to generate different and/or additional waveforms.

In existing manual, as opposed to robotic, electrosurgical systems, the surgeon can cause a driving electrosurgical signal with a particular waveform (e.g. COAG, CUT or BLEND) to be provided to an electrosurgical instrument attached to the electrosurgical generator using controls (e.g. buttons) on the manual electrosurgical instrument or using controls (e.g. foot pedals) connected to the electrosurgical generator. FIG. 3 illustrates an example manual monopolar electrosurgical instrument 302 that comprises at its distal end 304 an active electrode 306 for achieving a surgical effect when activated by a driving electrosurgical signal. The manual monopolar electrosurgical instrument 302 also comprises two activation buttons 308, 310 which can be used to cause the electrosurgical generator to provide a driving electrosurgical signal with a first waveform (e.g. a CUT waveform) and a driving electrosurgical signal with a second waveform (e.g. a COAG waveform) respectively to the electrosurgical instrument 302. The CUT button is typically coloured yellow and the COAG button is typically coloured blue to comply with specific standards.

FIG. 4 is used to explain how such a monopolar electrosurgical instrument 302 controls the operation of an electrosurgical generator 402. As shown in FIG. 4 the electrosurgical instrument 302 is attached to the electrosurgical generator 402 via a cable 404. Typically, the cable is integrated with the electrosurgical instrument 302 to form a single disposable device. However, the cable 404 may not be integral with the electrosurgical instrument, but the cable 404 may have a connector at one end which is configured to engage a corresponding connector of the electrosurgical instrument 302. In either case, the cable 404 typically comprises a connector at one end which is configured to engage a corresponding connector of the electrosurgical generator 402. This generator-end connector of the cable 404 may, for example, be a standard 3-pin Valleylab™ connector, such as that described in the Valleylab™ FT10 Energy Platform User Guide.

The cable 404 carries three conductors or wires 410, 412, 414—an active wire 410 and two control wires 412, 414. The active wire 410 is used to transmit a driving electrosurgical signal generated by the electrosurgical generator 402 to the electrosurgical instrument 302. The control wires 412, 414 are used to transmit activation signals generated by the electrosurgical instrument 302 to the electrosurgical generator 402.

The active wire 410 is electrically coupled to the active electrode 306 of the electrosurgical instrument 302 so that any driving electrosurgical signal received on the active wire 410 is provided to the active electrode 306. The two activation buttons 308, 310 of the electrosurgical instrument 302 are connected to corresponding switches 406, 408. One port of each switch 406, 408 is coupled to the active wire 410 and the other port of each switch 406, 408 is coupled to one of the control wires 412, 414. Specifically, a second port of the first switch 406 is coupled to the first control wire 412, and the second port of the second switch 408 is coupled to the second control wire 414. When an activation button 308, 310 is depressed the corresponding switch 406, 408 is activated which connects the active wire 410 to the corresponding control wire 412, 414 which sends a corresponding activation signal to the electrosurgical generator 402. Specifically, when the electrosurgical generator 402 is powered on, but is not active (i.e. is not generating a driving electrosurgical signal) the electrosurgical generator 402 outputs a weak signal on the active wire 410 and when a switch 406, 408 is activated that weak signal is transmitted on the corresponding control wire 412, 414.

When an activation signal is detected by control logic 416 of the electrosurgical generator the control logic 416 causes RF generation logic 418 of the electrosurgical generator 402 to output a driving electrosurgical signal on the active wire 410 with a waveform associated with that activation signal. For example, the first activation button 308 may be associated with a CUT waveform such that when the user presses or activates the first activation button 308 a first activation signal is transmitted to the electrosurgical generator 402 on the first control wire 412 which causes the electrosurgical generator 402 to output a driving electrosurgical signal with a CUT waveform on the active wire 410. The second activation button 310 may be associated with a COAG waveform such that when the user presses or activates the second activation button 310 a second activation signal is transmitted to the electrosurgical generator 402 on the second control wire 414 which causes the electrosurgical generator 402 to output a driving electrosurgical signal with a COAG waveform on the active wire 410. In this example, a separate return electrode 420 is directly connected to the electrosurgical generator 402 via a separate cable 422.

Instead of having the activation buttons on the electrosurgical instrument itself there may be a foot pedal system which allows the surgeon, or other user, to cause an electrosurgical generator to provide a driving electrosurgical signal with one waveform or another to an electrosurgical instrument attached to the electrosurgical generator. In some cases, using a separate foot pedal system is preferred as it reduces the complexity of the electrosurgical instrument. FIG. 5 illustrates an example foot pedal system 502 comprising a first foot pedal 504 and a second foot pedal 506 which can be used to cause an electrosurgical generator to provide a driving electrosurgical signal with a first waveform (e.g. a CUT waveform) and a second waveform (e.g. a COAG waveform) respectively to an electrosurgical instrument attached to the electrosurgical generator. FIG. 6 is used to explain how such a foot pedal system 502 can be used to control the operation of an electrosurgical generator 402 and an electrosurgical instrument 602.

The foot pedal system 502 is connected to the electrosurgical generator 402 via a cable 604. The cable 604 may be integral with the foot pedal system 502 or may be connectable to the foot pedal system 502 via a connector which engages a corresponding connector of the foot pedal system. In either case, the cable 604 typically comprises a connector that engages a corresponding connector of the electrosurgical generator 404. In these cases the cable 604 carries three conductors or wires 610, 612, 614—an active wire 610 and two control wires 612, 614.

The foot pedals 504 and 506 work in the same manner as the activation buttons 308, 310 of FIGS. 3-4. Specifically, the foot pedals 504, 506, like the activation buttons 308, 308, are each connected to a switch 606, 608. One port of each switch 606, 608 is coupled to the active wire 610 and a second port of each switch 606, 608 is coupled to one of the control wires 612, 614. In particular, the second port of the first switch 606 is coupled to the first control wire 612 and the second port of the second switch 608 is coupled to the second control wire 614. When a foot pedal 504, 506 is depressed the corresponding switch 606, 608 is activated which connects the active wire 610 to the corresponding control wire 612, 614 which causes a corresponding activation signal to be transmitted to the electrosurgical generator 402.

When an activation signal is detected by the control logic 416 of the electrosurgical generator 402, the control logic 326 causes the RF generation logic 418 of the electrosurgical generator 402 to output a driving electrosurgical signal with a waveform associated with that activation signal on the active wire 610. For example, the first foot pedal 504 may be associated with a CUT waveform such that when the user presses or activates the first foot pedal 504 a first activation signal is transmitted to the electrosurgical generator 402 on the first control wire 612. When the electrosurgical generator 402 detects the first activation signal, the electrosurgical generator 402 outputs a driving electrosurgical signal with a CUT waveform on the active wire 610. The second foot pedal 506 may be associated with a COAG waveform such that when the user presses or activates the second foot pedal 506 a second activation signal is transmitted to the electrosurgical generator 402 on the second control wire 614. When the electrosurgical generator 402 detects the second activation signal, the electrosurgical generator 402 outputs a driving electrosurgical signal with a COAG waveform on the active wire 610. In this example, a cable comprising a single wire used to carry the driving electrosurgical signal is then connected to the active electrode 616 of the electrosurgical instrument 602. Like the example in FIG. 4, a separate return electrode 420 is directly connected to the electrosurgical generator 402 via a separate cable 422.

While the activation buttons 308, 310 and foot pedals 504, 506 described above with respect to FIGS. 3-6 provide convenient and safe means for activating an electrosurgical instrument in a manual electrosurgical system where a surgeon, or other user, holds the electrosurgical instrument during surgery, they are typically not suitable or not convenient for activating an electrosurgical instrument in a robotic electrosurgical system. Specifically, robotic electrosurgical systems typically comprise a plurality of robotic arms, each of which can be attached to a different surgical instrument. A surgeon, or other user, can dynamically control any of the arms (and thus any of the surgical instruments attached thereto) via one or more input controllers (e.g. hand controllers) of a central command interface.

If an electrosurgical instrument in a robotic electrosurgical system comprised one or more activation buttons, as described with respect to FIGS. 3-4, the surgeon would either have to move away from the command interface to depress the appropriate button on the instrument, or, the surgeon, or other user, would have to instruct another person to do so, which may be unsafe (e.g. depressing the button may cause the instrument to move to an undesired position in the patient) and may cause unnecessary delays and errors. If, alternatively, a foot pedal system is connected to each electrosurgical generator, since there may be multiple generators that control different electrosurgical instruments the surgeon, or other user, may have to manually confirm that the correct pedal system is used. It would be much more convenient and safe if the surgeon, or other user, were able to activate an electrosurgical instrument attached to a robot arm via the command interface. Specifically, not only would it be more convenient to activate electrosurgical instruments from the command interface, but the system could ensure that the desired electrosurgical instrument was being activated.

The embodiments described below are provided by way of example only and are not limiting of implementations which solve any or all of the disadvantages of electrosurgical systems.

SUMMARY

This summary is provided to introduce a selection of concepts that are further described below in the detailed description. This summary is not intended to identify key features or essential features of the claimed subject matter, nor is it intended to be used to limit the scope of the claimed subject matter.

Described herein are electrosurgical connection units for a surgical robot arm to connect an electrosurgical instrument attached to the arm to an electrosurgical generator. The electrosurgical connection units include an input port connectable to the electrosurgical generator, the input port configured to receive a driving electrosurgical signal and output one or more activation signals; an output port connectable to the electrosurgical instrument, the output port configured to output the driving electrosurgical signal received on the input port; one or more activation switch units, wherein activation of an activation switch unit causes an activation signal to be output from the input port indicating a driving electrosurgical signal with a desired waveform is to be activated; and a control unit configured to selectively activate one of the one or more activation switch units in response to a control signal.

A first aspect provides an electrosurgical connection unit for a surgical robot arm, the electrosurgical connection unit comprising: an input port connectable to an electrosurgical generator, the input port configured to receive a driving electrosurgical signal and output one or more activation signals; an output port connectable to an electrosurgical instrument, the output port configured to output the driving electrosurgical signal received on the input port; one or more activation switch units, wherein activation of an activation switch unit causes an activation signal to be output from the input port indicating a driving electrosurgical signal with a desired waveform is to be activated; and a control unit configured to selectively activate one of the one or more activation switch units in response to a control signal.

The input port may be coupled to an active wire for receiving the driving electrosurgical signal and one or more control wires for transmitting an activation signal, and when an activation switch unit is activated the active wire is connected to one of the one or more control wires to generate the activation signal.

Each activation switch unit may comprise one or more switches in series wherein one end of the series of switches is coupled to the active wire and the other end of the series of switches is coupled to one of the one or more control wires.

At least one of the activation switch units may comprise at least two switches in series.

The one or more activation switch units may comprise a first activation switch unit and a second activation switch unit.

When the input port is connected to an electrosurgical generator, activating the first activation switch unit may cause a first activation signal to be transmitted to the electrosurgical generator which causes the electrosurgical generator to output a driving electrosurgical signal with a first waveform, and activating the second activation switch unit causes a second activation signal to be transmitted to the electrosurgical generator which causes the electrosurgical generator to output a driving electrosurgical signal with a second waveform.

The desired waveform may be one waveform of a plurality of waveforms supported by the electrosurgical generator. The plurality of waveforms supported by the electrosurgical generator may comprise a cutting waveform for producing a cutting effect and a coagulating waveform for producing a coagulating effect.

The input port may be configured to receive a single cable over which the driving electrosurgical signal is received from the electrosurgical generator and the one or more activation signals are transmitted to the electrosurgical generator.

The output port may be configured to receive a cable over which the driving electrosurgical signal is transmitted to the electrosurgical instrument.

The output port may be further configured to receive a return electrosurgical signal from the electrosurgical instrument or a return electrode, and the input port is configured to output a return electrosurgical signal received on the output port.

The return electrosurgical signal may also be transmitted to the electrosurgical generator over the single cable received by the input port.

The input port may be further configured to receive a second cable over which the return electrosurgical signal is transmitted to the electrosurgical generator.

The output port may be configured to receive a second cable over which the return electrosurgical signal is received from a return electrode.

The control unit may be configured to activate an activation switch unit by outputting one or more signals that cause the activation switch unit to be activated.

The electrosurgical connection unit may further comprise an isolation device that forms an isolation barrier between the one or more activation switch units and the control unit.

The isolation device may be a digital isolator.

The electrosurgical connection unit may further comprise an alternating current coupling circuit situated between the control unit and each of the one or more activation switch units, each alternating current coupling circuit configured to receive a signal output by the control unit and generate a direct current filtered version of the signal.

The electrosurgical connection unit may further comprise a measurement unit configured to measure a parameter of an activation switch unit and output measurement information to the control unit, the measurement information enabling a determination to be made as whether the activation switch unit is operating as expected.

The measurement unit may be an impedance measurement device configured to measure an impedance across the activation switch unit The electrosurgical connection unit may further comprise a capacitance emulation unit configured to present a predetermined capacitance to the electrosurgical generator when the electrosurgical generator is connected to the input port and activation of an activation switch unit of the one or more activation switch units causes an activation signal to be transmitted to the electrosurgical generator.

The control unit may be configured to generate a token comprising information indicating a time at which the token was generated and transmit the token to an external computing device, and the control signal is a modified version of the token that further comprises information indicating the desired waveform.

The control unit may be configured to only activate an activation switch unit of the one or more activation switch units in response to receiving the modified version of the token when at the time the modified version of the token is received at the control unit an elapsed time since the token was generated is less than a threshold.

A second aspect provides a surgical robot arm comprising the electrosurgical connection unit of the first aspect.

The electrosurgical connection unit may be integral with the surgical robot arm

The electrosurgical connection unit may be removably attached to the surgical robot arm.

A third aspect provides a surgical robotic system comprising: the surgical robot arm of the second aspect; an electrosurgical generator connected to the input port of the electrosurgical connection unit; and an electrosurgical instrument connected to the output port of the electrosurgical connection unit.

A fourth aspect provides a method of activating an electrosurgical instrument attached to a surgical robot arm, the method comprising: generating, at a surgical robot arm control unit, a token comprising information indicating a time at which the token was generated; transmitting the token from the surgical robot arm control unit to an external computing device; receiving the token at the external computing device; in response to the external computing device receiving input indicating that the electrosurgical instrument is to be activated, transmitting a modified version of the received token to the surgical robot arm control unit, the modified version of the token indicating that the electrosurgical instrument is to be activated; and if the surgical robot arm control unit receives the modified version of the token within a threshold amount of time from when the token was generated, outputting one or more signals that cause the electrosurgical instrument to be activated.

The method may further comprise periodically incrementing a rolling counter at the surgical robot arm control unit, and the information indicating the time at which the token was generated comprises a value of the counter at the time the token was generated.

The method may further comprise comparing the information in the modified version of the token indicating the time at which the token was generated to a current value of the counter to determine whether the modified version of the token was received within the threshold amount of time from when the token was generated.

The token may further comprise information uniquely identifying the surgical robot arm, and the method may further comprise determining whether the modified version of the token comprises the information uniquely identifying the surgical robot arm, and only outputting the one or more signals it is determined that the modified version of the token comprises the information uniquely identifying the surgical robot arm.

The token may further comprise validation information indicating whether the token is valid, and the method may further comprise determining from the validation information in the modified version of the token if the modified version of the token is valid, and only outputting the one or more signals when it is determined that the modified version of the token is valid.

The validation information may be an error detection code.

The validation information may be a cyclic redundancy check code.

The method may further comprise, determining, at the external computing device, whether the modified version of the token is valid from the validation information; and only transmitting the modified version of the token to the surgical robot arm control unit when it is determined that the modified version of the token is valid.

The modified version of the token may comprise modified validation information.

The modified version of the token may comprise information indicating a waveform of a driving electrosurgical signal to activate the electrosurgical instrument.

The waveform may be one of a monopolar coagulation waveform, a monopolar cut waveform, a bipolar coagulation waveform, a bipolar cut waveform and a blend waveform.

The one or more signals output by the surgical robot arm control unit may cause the electrosurgical instrument to be activated by a driving electrosurgical signal with the waveform indicated in the modified version of the token.

The method may further comprise determining whether the electrosurgical instrument supports the waveform indicated in the modified version of the token, and only transmitting the modified version of the token to the surgical robot arm control unit if it is determined that the electrosurgical instrument supports the waveform indicated in the modified version of the token.

The method may further comprise determining whether the surgical robot arm is currently being controlled by a user, and only transmitting the modified token to the surgical robot arm control unit if it is determined that the surgical robot arm is currently being controlled by a user.

The modified version of the token may be transmitted from the external computing device to the surgical robot arm control unit via one or more processors, and the method may further comprise, if any of the one or more processor detects a non-electrosurgical activation state when the modified version of the token is received at that processor, discarding or invalidating the modified version of the token.

The external computing device may receive input indicating that the electrosurgical instrument is to be activated when a user activates an input on a device used to control the surgical robot arm and the modified version of the token is only transmitted to the surgical robot arm control unit if it is detected that the device is currently being used to control the surgical robot arm.

The method may further comprise, in response to receiving the modified version of the token, determining at the surgical robot arm control unit whether the electrosurgical instrument and/or the surgical robot arm are in a suitable state for electrosurgical activation, and the one or more signals are only output if it is determined that the electrosurgical instrument and/or surgical robot arm are in a suitable state for electrosurgical activation.

The one or more control signals output by the surgical robot arm control unit may be provided to an activation switch unit which causes activation of the activation switch unit, wherein activation of the activation switch unit causes an activation signal to be transmitted to an electrosurgical generator.

The one or more signals output by the surgical robot arm control unit may comprise an oscillating signal.

The one or more signals output by the surgical robot arm control unit may comprise a square wave.

A fifth aspect provides a system to activate an electrosurgical instrument attached to a surgical robot arm, the system comprising: an external computing device configured to: receive a token from a surgical robot arm control unit, the token comprising information indicating a time at which the token was generated by the surgical robot arm control unit; and in response to receiving input indicating that the electrosurgical instrument is to be activated, transmit a modified version of the token to the surgical robot arm control unit, the modified version of the token indicating that the electrosurgical instrument is to be activated; and the surgical robot arm control unit in communication with the external computing device, the surgical robot arm control unit configured to: receive the modified version of the token; and in response to the modified version of token being received within a threshold amount of time from when the token was generated, outputting one or more signals that cause the electrosurgical instrument to be activated.

The above features may be combined as appropriate, as would be apparent to a skilled person, and may be combined with any of the aspects of the examples described herein.

BRIEF DESCRIPTION OF THE DRAWINGS

Examples will now be described in detail with reference to the accompanying drawings in which.

Figure 1:
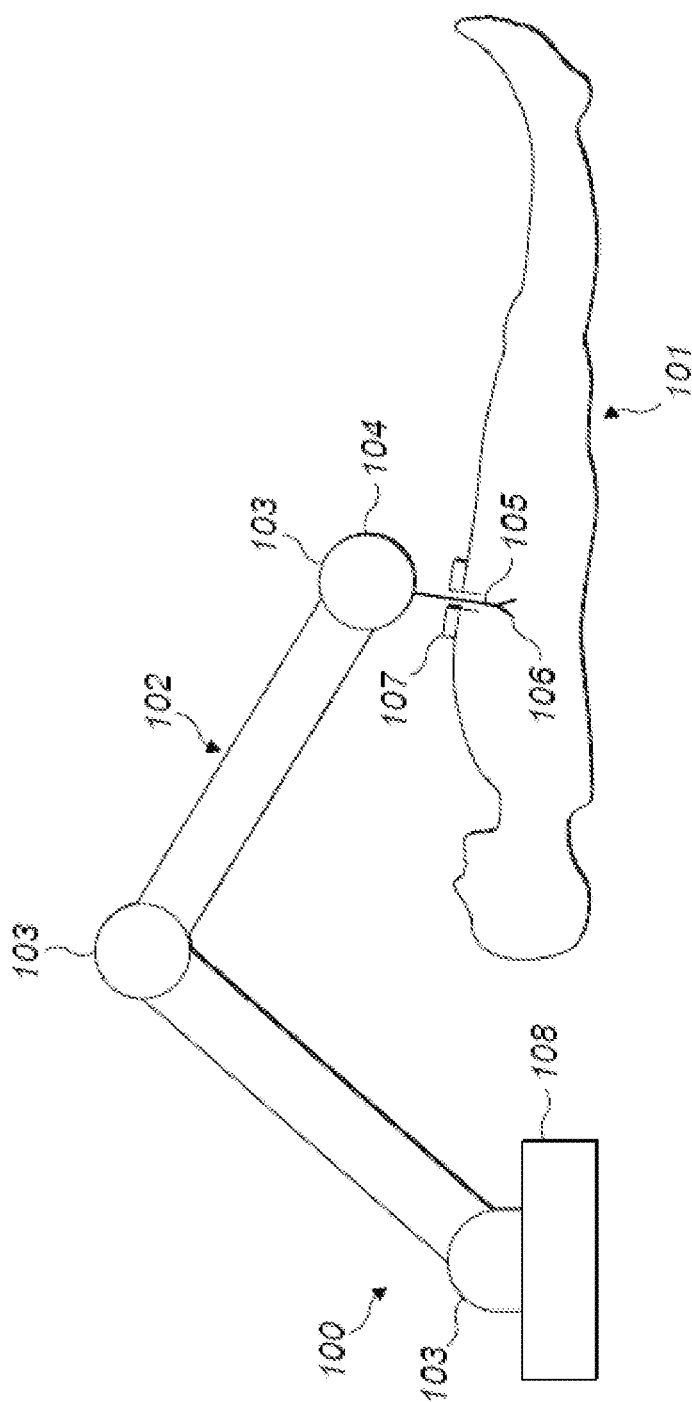
FIG. 1 is a schematic diagram of an example surgical robot performing a surgical procedure.

The accompanying drawings illustrate various examples. The skilled person will appreciate that the illustrated element boundaries (e.g., boxes, groups of boxes, or other shapes) in the drawings represent one example of the boundaries. It may be that in some examples, one element may be designed as multiple elements or that multiple elements may be designed as one element. Common reference numerals are used throughout the figures, where appropriate, to indicate similar features.

DETAILED DESCRIPTION

The following description is presented by way of example to enable a person skilled in the art to make and use the invention. The present invention is not limited to the embodiments described herein and various modifications to the disclosed embodiments will be apparent to those skilled in the art. Embodiments are described by way of example only.

Described herein are electrosurgical connection units for a surgical robot arm for connecting an electrosurgical instrument attached to the arm to an electrosurgical generator in a manner that allows the electrosurgical instrument to be dynamically driven by a desired waveform. Specifically, the electrosurgical connection units described herein comprise an input port connectable to an electrosurgical generator and an output port connectable to an electrosurgical instrument attached to the arm. The electrosurgical connection unit is configured to receive a driving electrosurgical signal via the input port and transmit one or more activation signals via the input port. The input port and the output port are connected such that any driving electrosurgical signal received on the input port is output on the output port. The electrosurgical connection units also comprise one or more activation switch units. When an activation switch unit is activated it causes an activation signal to be transmitted to the electrosurgical generator via the input port. The activation signal indicates a driving electrosurgical signal with a desired waveform from a plurality of waveforms is to be activated by the electrosurgical generator. The electrosurgical connection units also comprise a control unit which is configured to activate one of the one or more activation switch units in response to receiving one or more control signals (which may be generated in response to input from the surgeon or other user indicating that the electrosurgical instrument is to be activated by a driving electrosurgical signal with a desired waveform).

Figure 7:
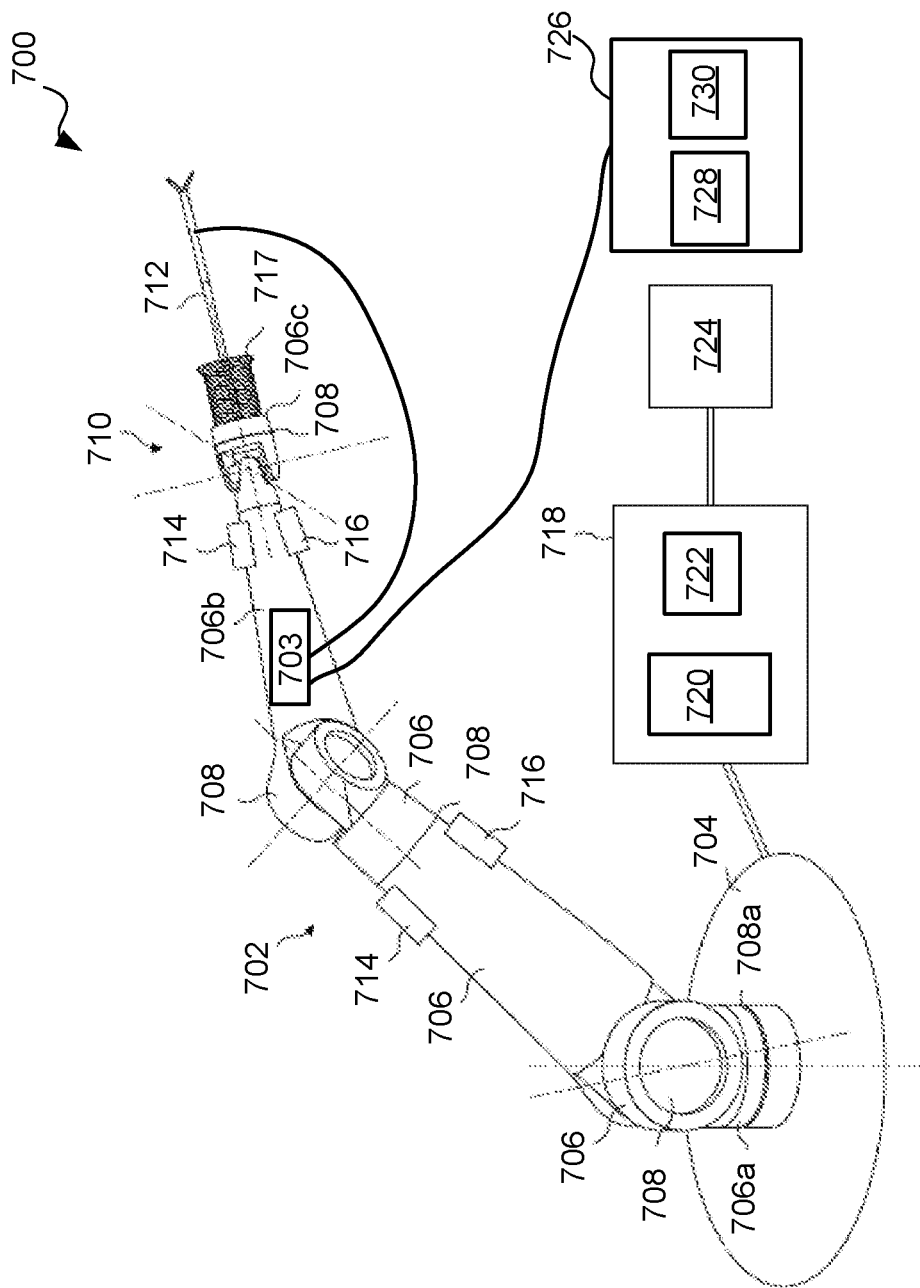
FIG. 7 is a schematic diagram of an example surgical robot system including a robot arm comprising an electrosurgical connection unit.

Reference is now made to FIG. 7 which shows an example surgical robot system 700 in which the electrosurgical connection units described herein may be implemented. The system 700 comprises a robot arm 702 which comprises an electrosurgical connection unit 703 for connecting an electrosurgical instrument attached to the arm to an electrosurgical generator.

The robot arm 702 extends from a proximal end attached to a base 704. The arm comprises a number of rigid links 706. The links are coupled by revolute joints 708. The most proximal link 706a is coupled to the base by joint 708a. It and the other links are coupled in series by further ones of the joints 708. Suitably, a wrist 710 is made up of four individual revolute joints. The wrist 710 couples one link (706b) to the most distal link (706c) of the arm. The most distal link 706c is at the distal end of the arm and carries an attachment structure 717 for a surgical instrument 712. Each joint 708 of the arm has one or more motors 714 which can be operated to cause rotational motion at the respective joint, and one or more position and/or torque sensors 716 which provide information regarding the current configuration and/or load at that joint. The motors may be arranged proximally of the joints whose motion they drive, so as to improve weight distribution. For clarity, only some of the motors and sensors are shown in FIG. 7. The arm may be generally as described in our co-pending patent application PCT/GB2014/053523.

The arm terminates in an attachment structure 717 for interfacing with the instrument 712. The instrument 712 may take the form described with respect to FIG. 2. The attachment structure 717 comprises a drive assembly for driving articulation of the instrument. Movable interface elements of the drive assembly interface mechanically engage corresponding movable interface elements of the instrument interface in order to transfer drive from the robot arm to the instrument. One instrument is exchanged for another several times during a typical operation. Thus, the instrument is attachable and detachable from the robot arm during the operation. Features of the drive assembly interface and the instrument interface aid their alignment when brought into engagement with each other, so as to reduce the accuracy with which they need to be aligned by the user.

The instrument 712 comprises an end effector for performing an operation. The end effector may take any suitable form. For example, the end effector may be smooth jaws, serrated jaws, a gripper, a pair of shears, a needle for suturing, a camera, a laser, a knife, a stapler, a cauteriser, a suctioner.

A variety of instrument types are known, each adapted to perform a particular surgical function. One example type of instrument is an electrosurgical instrument which is adapted to perform an electrosurgical function. As described above, electrosurgery is the passing of a high frequency (i.e. radio frequency) current through tissue to cause a desired effect (e.g. cutting the tissue or coagulating the tissue). There are two types of electrosurgery—monopolar and bipolar. In monopolar electrosurgery the high frequency current passes through the patient from a live or active electrode of the electrosurgical instrument to a separate return electrode placed on the patient, which may also be referred to as a dispersive electrode pad, a grounding pad, a neutral electrode, a grounding mat, an indifferent electrode or a patient electrode. In bipolar electrosurgery the active and return electrodes are both within the electrosurgical instrument and the current passes through the patient from the active electrode of the electrosurgical instrument to the return electrode of the electrosurgical instrument. An electrosurgical instrument which is configured for monopolar electrosurgery (e.g. an electrosurgical instrument that comprises an active electrode only) will be referred to herein as a monopolar electrosurgical instrument, and an electrosurgical instrument which is configured for bipolar electrosurgery (e.g. an electrosurgical instrument that comprises both an active electrode and a return electrode) will be referred to herein as a bipolar electrosurgical instrument.

Figure 2:
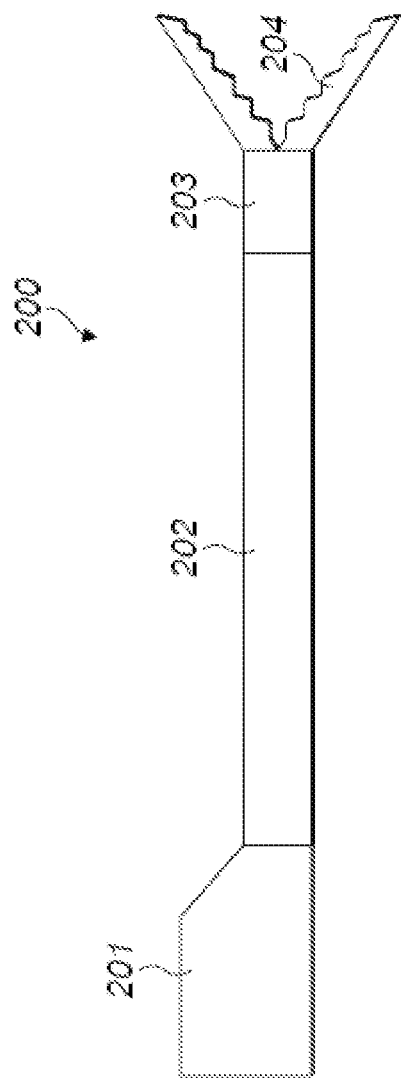
FIG. 2 is a schematic diagram of an example surgical instrument.

As described with respect to FIG. 2 the instrument comprises an articulation between the instrument shaft and the end effector. The articulation comprises several joints which permit the end effector to move relative to the shaft of the instrument. The joints in the articulation are actuated by driving elements, such as cables. These driving elements are secured at the other end of the instrument shaft to the interface elements of the instrument interface. Thus, the robot arm transfers drive to the end effector as follows: movement of a drive assembly interface element moves an instrument interface element which moves a driving element which moves a joint of the articulation which moves the end effector.

Controllers for the motors, torque sensors and encoders are distributed with the robot arm. The controllers are connected via a communication bus to a robot control unit 718. The robot control unit 718 comprises a processor 720 and a memory 722. Memory 722 stores in a non-transient way software that is executable by the processor 720 to control the operation of the motors 714 to cause the arm 702 to operate in the manner described herein. In particular, the software can control the processor 720 to cause the motors (for example via distributed controllers) to drive in dependence on inputs from the sensors 716 and from a surgeon command interface 724. The robot control unit 718 is coupled to the motors 714 for driving them in accordance with outputs generated by execution of the software. The robot control unit 718 is coupled to the sensors 716 for receiving sensed input from the sensors, and to the command interface 724 for receiving input from it. The respective couplings may, for example, each be electrical or optical cables, or may be provided by a wireless connection. The command interface 724 comprises one or more input devices whereby a user can request motion of the end effector in a desired way. The input devices could, for example, be manually operable mechanical input devices such as hand controllers or joysticks, or contactless input devices such as optical gesture sensors. The software stored in memory 722 is configured to respond to those inputs and cause the joints of the arm and instrument to move accordingly, in compliance with a pre-determined control strategy. The control strategy may include safety features which moderate the motion of the arm and instrument in response to command inputs. Thus, in summary, a surgeon at the command interface 724 can control the instrument 712 to move in such a way as to perform a desired surgical procedure. The robot control unit 718 and/or the command interface 724 may be remote from the arm 702.

The robot arm 702 also comprises an electrosurgical connection unit 703 for connecting an electrosurgical instrument 712 attached to the arm to an electrosurgical generator 726. As described above, electrosurgical instruments are driven by a high frequency current which may be referred to herein as a driving electrosurgical signal. The driving electrosurgical signals are generated by an electrosurgical generator 726, which may also be referred to as an electrosurgery generator, electrosurgical end unit, electrosurgery end unit, or ESU. Electrosurgical generators are generally capable of generating multiple different current waveforms to achieve different surgical effects. For example, many standard electrosurgical generators can be configured to generate COAG, CUT and BLEND waveforms. The COAG waveform consists of bursts of radio frequency, which when used at a low power setting causes a desiccation effect, and when used at a high-power setting causes a fulguration effect. The CUT waveform is a continuous waveform at a lower voltage, but higher current than COAG, which causes the tissue to be cut. A BLEND waveform is essentially a CUT waveform with a lower duty cycle. For example, the duty cycle of a CUT waveform is typically between 15% and 75%, whereas a CUT waveform typically has a duty cycle greater than 75%. The off time allows the tissue to cool creating some haemostasis. Accordingly, a BLEND waveform is typically used where haemostasis is required as tissue is cut. It will be evident to a person of skill in the art that these are examples only and that different electrosurgical generators may be configured to generate different and/or additional waveforms.

The electrosurgical generator 726 comprises any suitable means for configuring the waveforms that can be generated. For example, an electrosurgical generator 726 may comprise a user interface that comprises, for example, switches, buttons, dials etc., which enable a user to configure each supported waveform (e.g. a CUT waveform, a COAG waveform and a BLEND waveform). In other examples, the electrosurgical generator 726 may be configured electronically, such as via a control signal transmitted to the electrosurgical generator from a computing device. For example, the electrosurgical generator 726 may be connected to the robot control unit 718 and the waveforms configured by the command interface 724. The user may be able to configure, for example, the voltage and/or frequency of the waveform.

The electrosurgical generator 726 also comprises control logic 728 which is configured to receive activation signals indicating which waveform of the plurality of supported waveforms are to be activated by the electrosurgical generator 726. For example, where the electrosurgical generator 726 can generate a driving electrosurgical signal with a CUT waveform or a driving electrosurgical signal with a COAG waveform the electrosurgical generator 726 may be configured to receive one or more activation signals indicating which of the CUT waveform and the COAG waveform is to be used to generate the driving electrosurgical signal. In response to the control logic 728 detecting an activation signal indicating that a driving electrosurgical signal with a CUT waveform is to be activated the electrosurgical generator 726 (e.g. the RF generation logic 730) outputs a driving electrosurgical signal with a CUT waveform (as previously configured). Similarly, in response to the control logic 728 detecting an activation signal indicating that a driving electrosurgical signal with a COAG waveform is to be activated the electrosurgical generator 726 (e.g. the RF generation logic 730) outputs a driving electrosurgical signal with a COAG waveform (as previously configured). In some cases, the electrosurgical generator 726 may be configured to continue outputting a driving electrosurgical signal with the desired waveform so long as it detects the corresponding activation signal (and a fault condition has not been detected), and to cease outputting a driving electrosurgical signal with the desired waveform as soon as it ceases to detect the corresponding activation signal.

When an activation signal is detected by the control logic 728, in addition to causing a driving electrosurgical signal with the desired waveform to be output, the control logic 728 may cause a feedback signal to be output to alert the user of the activation of a particular waveform. The feedback may be in the form of visual feedback (e.g. an indicator light on a display panel of the electrosurgical generator 726) or audible feedback (e.g. a tone).

The electrosurgical connection unit 703 is configured to act as an intermediary between an electrosurgical instrument 712 attached to the arm 702 and an electrosurgical generator 726. Specifically, the electrosurgical connection unit 703 is configured to selectively transmit activation signals to the electrosurgical generator indicating that the electrosurgical instrument attached to the arm is to be activated by a driving electrosurgical signal with a particular waveform (of the plurality of waveforms supported by the electrosurgical generator) in response to one or more control signals received from an external computing device. The control signals may be generated by, for example, the robot control unit 718 in response to the surgeon or other user providing input via the command interface 724 indicating that the electrosurgical instrument attached to the arm currently being controlled is to be driven by a driving electrosurgical signal with a desired waveform. The electrosurgical connection unit 703 is also configured to receive any driving electrosurgical signal produced by the electrosurgical generator in response to an activation signal and provide the received driving electrosurgical signal to the electrosurgical instrument attached to the arm. Example electrosurgical connection units 703 are described below with respect to FIGS. 8-11.

The electrosurgical connection unit 703 may be integral with the arm 702 or may be removably attached to the arm 702. The electrosurgical connection unit 703 may be removably attached to the arm 702 using any suitable means such as, but not limited to, Velcro™, or gaffer tape. Although the electrosurgical connection unit 703 is shown in FIG. 7 as being attached to a middle link 706b of the arm 702, the electrosurgical connection unit 703 may be attached to any suitable part of the arm 702. For example, the electrosurgical connection unit 703 may be connected to any link 706a, 706b, 706c of the arm 702 or the electrosurgical connection unit 703 may be connected to the base 704 of the arm 702. In some cases the base 704 may comprise or be attached to a cart or trolley and the electrosurgical connection unit may be integral with or removably attached to the cart. The arm 702 is typically covered in a sterile drape during surgery. Where there is an opening in the drape around the base 704 of the arm 702, attaching the electrosurgical connection unit 703 to the base 704 or the most proximal link 706a may make it easier to connect the electrosurgical connection unit 703 to the electrosurgical generator 726 and/or the electrosurgical instrument 712 via the opening in the drape. In some cases, components of the electrosurgical connection unit 703 may be attached to different parts of the arm 702. For example, as described below, the electrosurgical connection unit may comprise an input port, and output port, one or more activation switches and a control unit. In some cases, the control unit may be situated on a different part of the arm from the input port, output port, and activation switches.

Figure 8:
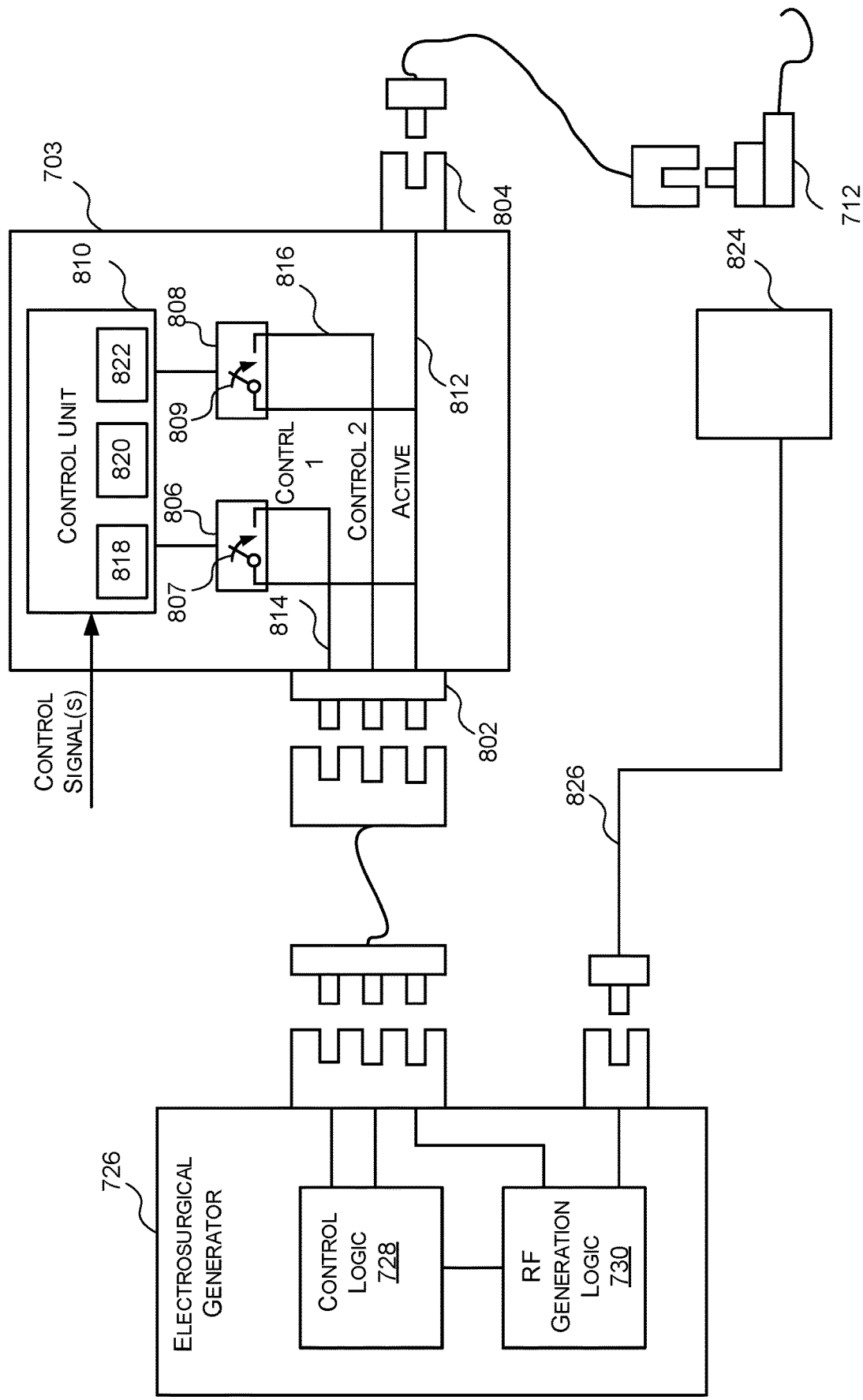
FIG. 8 is a block diagram of an example electrosurgical system comprising a first example electrosurgical connection unit for a monopolar electrosurgical instrument.

Reference is now made to FIG. 8 which illustrates an example electrosurgical connection unit 703 for connecting a monopolar electrosurgical instrument to an electrosurgical generator 726. The electrosurgical connection unit 703 comprises an input port 802, an output port 804, a plurality of activation switch units 806, 808 and a control unit 810.

The input port 802 is connectable (directly or indirectly) to an electrosurgical generator 726 so as to receive a driving electrosurgical signal generated by the electrosurgical generator 726 and to transmit one or more activation signals to the electrosurgical generator 726. Each activation signal indicates to the electrosurgical generator 726 that a driving electrosurgical signal with a desired waveform of the plurality of waveforms supported by the electrosurgical generator 726 is to be activated. The input port 802 may be electrically coupled to a plurality of wires or conductors—an active wire or conductor 812 to receive the driving electrosurgical signal from the electrosurgical generator 726 and one or more control wires or conductors 814, 816 to transmit the activation signals(s) to the electrosurgical generator 726. In the example shown in FIG. 8, there are two control wires 814, 816, one control wire 814 is configured to transmit a first activation signal to the electrosurgical generator 726 that indicates that a driving electrosurgical signal with a first waveform (e.g. a CUT waveform) is to be activated and the other control wire 816 is configured to transmit a second activation signal to the electrosurgical generator 726 that indicates that a driving electrosurgical signal with a second waveform (e.g. a COAG waveform) is to be activated. However, it will be evident to a person of skill in the art that this is an example only and that there may be fewer than two control wires and/or more than two control wires over which the activation signal(s) are transmitted.

The input port 802 may be configured to receive one or more cables over which the driving electrosurgical signal is received from the electrosurgical generator 726 and the activation signals are transmitted to the electrosurgical generator 726. In some cases, the input port 802 may be configured to receive a single cable over which the driving electrosurgical signal and the activation signals are transmitted. In other cases, the input port 802 may be configured to receive a plurality of cables over which the driving electrosurgical signal and the activation signal are transmitted. For example, there may be one cable per signal. In some cases, the input port 802 may comprise one connector for each expected cable that is configured to engage a corresponding connector of the cable. In some cases, the connector(s) of the input port 802 may be male connectors which are configured to receive a corresponding female connector of a cable connected directly or indirectly to the electrosurgical generator 726.

The output port 804 is connectable (directly or indirectly) to an electrosurgical instrument 712 attached to the arm 702. The output port 804 is electrically connected or coupled to the active wire 812 so that any driving electrosurgical signal received from the electrosurgical generator 726 via the input port 802 is output on the output port 804.

The output port 804 may be configured to receive a cable over which the driving electrosurgical signal is transmitted to the electrosurgical instrument 712. In some examples, the output port 804 comprises a female connector configured to engage a corresponding male connector connected to a cable which is connected directly or indirectly to the electrosurgical instrument 712.

Each activation switch unit 806, 808 is configured to, when activated, cause an activation signal to be transmitted via the input port 802 to indicate to the electrosurgical generator 726 that a driving electrosurgical signal with a desired waveform, of the plurality of waveforms supported by the electrosurgical generator 726, is to be activated. In response to detecting the activation signal, the electrosurgical generator 726 outputs a driving electrosurgical signal with the desired waveform. The input port 802 then receives the driving electrosurgical signal with the desired waveform and outputs the received signal on the output port 804.

In the example of FIG. 8 there are two activation switch units 806 and 808. When the first activation switch unit 806 is activated a first activation signal is transmitted over the first control wire 814 which indicates to the electrosurgical generator 726 that a driving electrosurgical signal with a first desired waveform (e.g. CUT waveform) is to be activated. In response to detecting the first activation signal, the electrosurgical generator 726 generates and outputs a driving electrosurgical signal with the desired waveform (e.g. CUT waveform). When the second activation switch unit 808 is activated a second activation signal is transmitted over the second control wire 816 which indicates to the electrosurgical generator 726 that a driving electrosurgical signal with a second desired waveform (e.g. COAG waveform) is to be activated. In response to detecting the second activation signal the electrosurgical generator 726 generates and outputs a driving electrosurgical signal with the second desired waveform (e.g. COAG waveform). However, it will be evident to a person of skill in the art that this is an example only and that there may be more than two activation switch units or only one activation switch unit (see, for example, FIG. 11).

Figure 4:
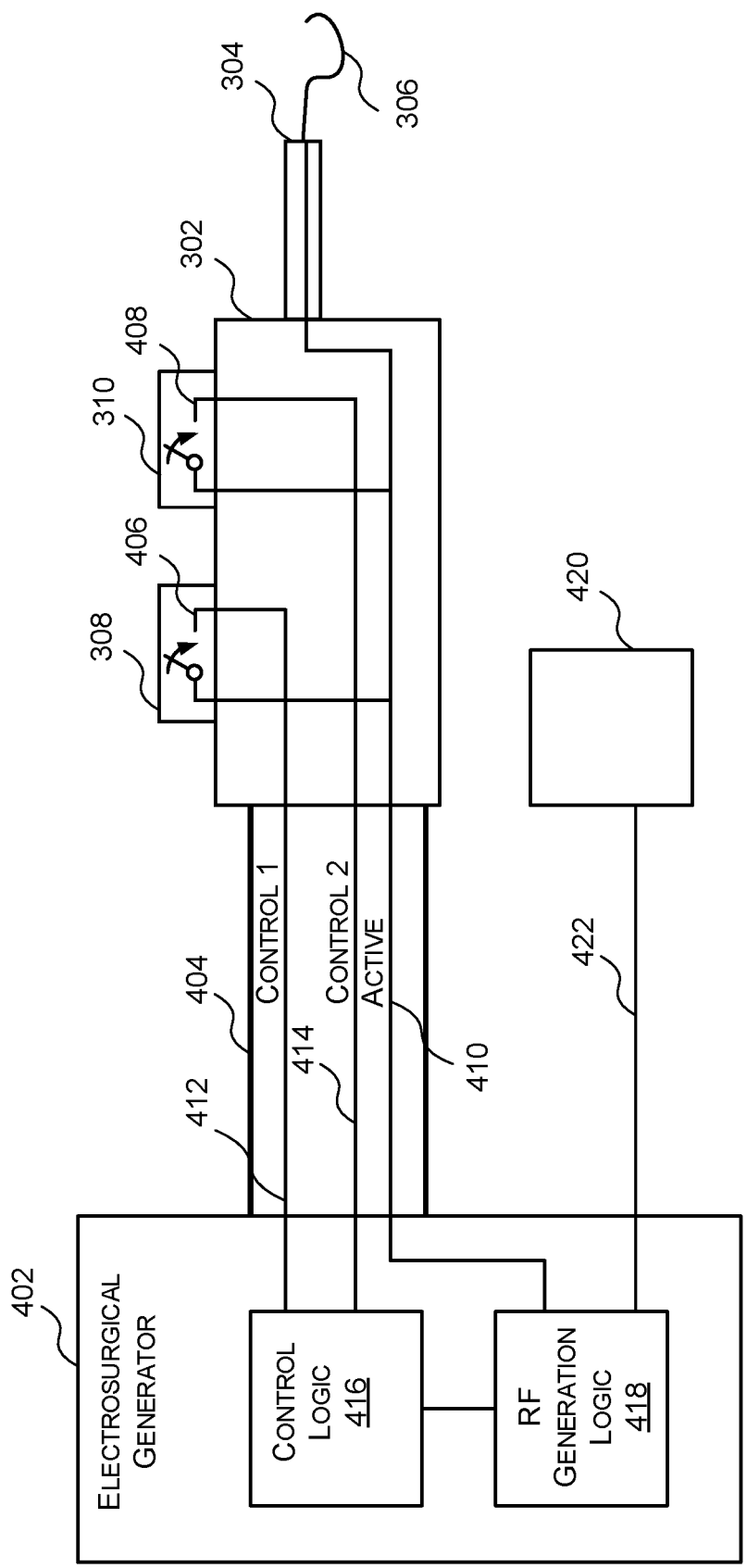
FIG. 4 is a block diagram of an example electrosurgical system comprising the monopolar electrosurgical instrument of FIG. 3, an electrosurgical generator and a return electrode.
Figure 6:
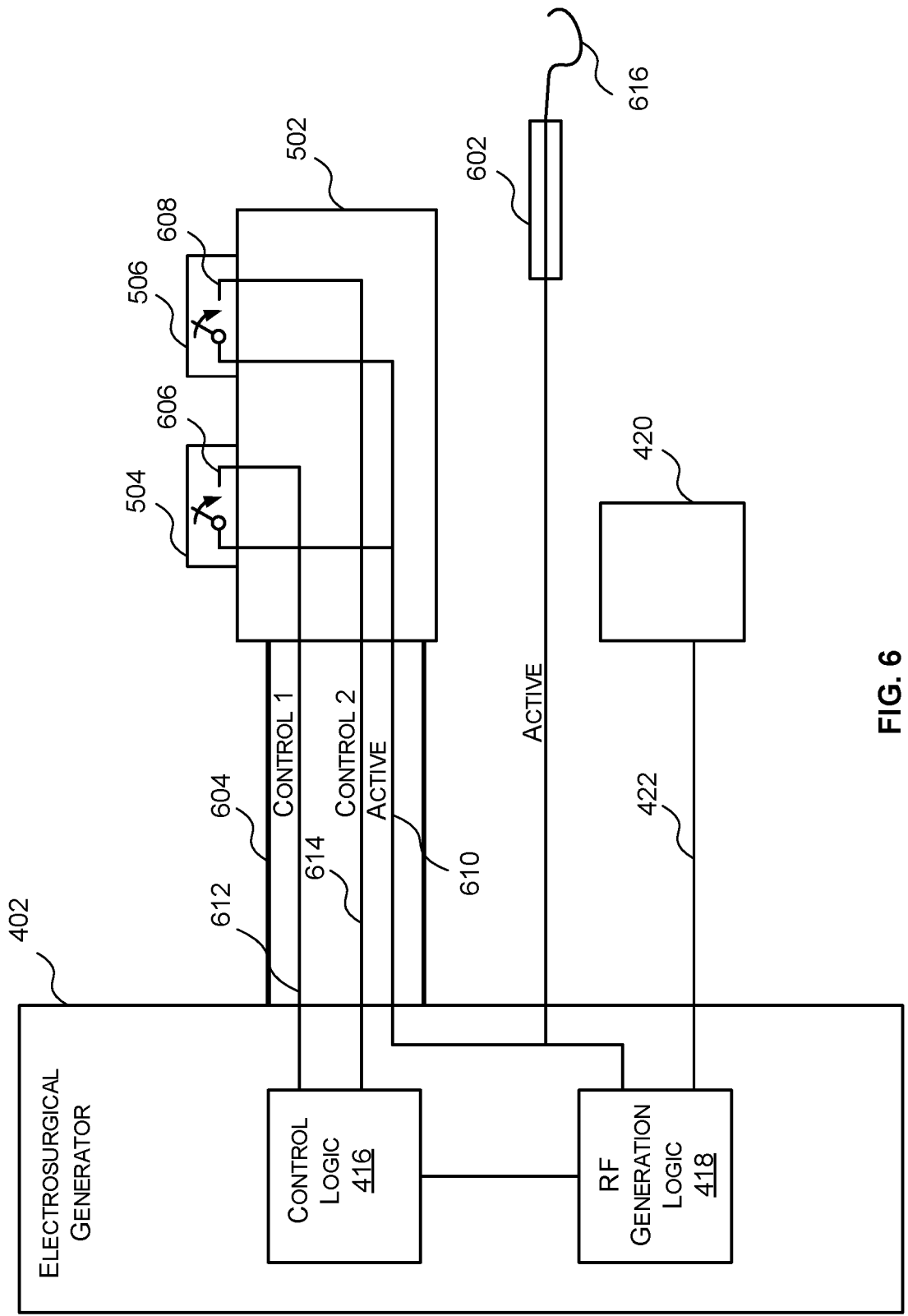
FIG. 6 is a block diagram of an example electrosurgical system comprising the foot pedal system of FIG. 5, a monopolar electrosurgical instrument, an electrosurgical generator and a return electrode.

In the example shown in FIG. 8, a first port of each activation switch unit 806, 808 is connected to the active wire 812 and a second port of each activation switch unit 806, 808 is connected to one of the control wires 814, 816. Specifically, the second port of the first activation switch unit 806 is connected to the first control wire 814, and the second port of the second activation switch unit 808 is connected to the second control wire 816. In this example, when an activation switch unit 806, 808 is activated the active wire 812 is electrically connected to the corresponding control wire 814, 816 (i.e. the active wire 812 is shorted to the corresponding control wire 814, 816) which causes an activation signal to be transmitted to the electrosurgical generator on that control wire 814, 816. In other words, when an activation switch unit 806, 808 is activated it closes a control loop extending between the electrosurgical generator 726 and the electrosurgical connection unit 703 which can be detected by the electrosurgical generator 726 (e.g. control logic 728 of the electrosurgical generator 726). When the electrosurgical connection unit 703 is configured to generate the activation signals in this manner the electrosurgical connection unit 703 can be connected to existing electrosurgical generators, such as those described above with reference to FIGS. 4 and 6, which are configured to detect activation signals by detecting a closure of a control loop.

Each activation switch unit 806, 808 comprises at least one switch 807, 809 connected in series with the first port and the second port of the activation switch unit 806, 808. When an activation switch unit 806, 808 is activated all the switch(es) 807, 809 of the activation switch unit 806, 808 are placed in the closed position so as to connect the first and second ports of the activation switch unit 806, 808. In the example of FIG. 8 each activation switch unit 806, 808 comprises one switch 807, 809. However, in other examples, one or more of the activation switch units 806, 808 may comprise a plurality of switches in series. Having multiple switches in series prevents an activation signal inadvertently being transmitted by the electrosurgical connection unit 703 to the electrosurgical generator when one of the switches fails in the closed position, causing a driving electrosurgical signal to be inadvertently provided to an electrosurgical instrument attached to the arm. Causing an electrosurgical instrument to be inadvertently activated could be extremely dangerous. Each switch may be implemented, for example, by a relay, such as an electromechanical relay (EMR) or a solid-state relay (SSR). As is known to those of skill in the art, in electromechanical relays (EMR), contacts are opened or closed by a magnetic force. With solid-state relays (SSR), there are no contacts and switching is electronic.

The control unit 810 is configured to control the activation switch units 806, 808 in response to control signals received from an external computing device. Specifically, the control unit 810 is configured to receive control signals from an external computing device and selectively activate one of the activation switch units 806, 808 in response to the control signals so as to cause an electrosurgical instrument attached to the arm to be driven by a driving electrosurgical signal with a desired waveform. The control signals may be generated by an external computing device in response to input received from a surgeon or another user indicating that the electrosurgical instrument attached to a particular arm is to be activated by a driving electrosurgical signal with a particular waveform. In some cases, the control signals may be generated by the robot control unit 718 in response to input received from the surgeon or another user via the command interface 724 indicating that the electrosurgical instrument attached to a particular arm is to be activated by a driving electrosurgical signal with a particular waveform.

In these cases, the command interface 724 may comprise one or more input devices that allow the user to indicate that an electrosurgical instrument that a user is currently controlling is to be activated by a driving control signal and what type of waveform. For example, where the command interface 724 comprises manually operable input devices such as hand controllers or joysticks, the hand controllers or joysticks may comprise one or more buttons, switches, or the like that allow the user to indicate that the electrosurgical instrument that is currently being controlled is to be activated by a driving electrosurgical signal and the type of waveform. For example, the hand controllers or joysticks may comprise a CUT button and a COAG button which the user can press to indicate that the electrosurgical instrument is to be activated by a CUT waveform or a COAG waveform. In some cases, to avoid a driving electrosurgical signal from being transmitted to an electrosurgical instrument by inadvertent contact with such buttons or switches, the one or more buttons or switches may only be able to cause a driving electrosurgical signal to be transmitted to the electrosurgical generator if the robot control unit detects that a user is currently grasping the hand controllers or joysticks.

In other examples, when the user is controlling an electrosurgical instrument the user may be provided with one or more options on a graphical user interface displayed on a display screen that can be clicked, or otherwise selected, by the user to indicate that the electrosurgical instrument is to be activated and the type of waveform the electrosurgical instrument is to be activated with. For example, a CUT button and a COAG button may displayed on a display screen that can be clicked, or otherwise selected, by the user to indicate that the electrosurgical instrument is to be activated with a CUT waveform or a COAG waveform.

In yet other examples, the command interface 724 may comprise a combination of the buttons and graphical user interface components described above to allow the user to indicate that a particular electrosurgical instrument is to be activated and the waveform to be used for the driving electrosurgical signal. For example, the user interface may allow the surgeon, or other user, to indicate the type of waveform to be used for the driving electrosurgical signal and the electrosurgical instrument to be activated, and the hand controller or joysticks may comprise a single button which, when depressed, indicates that the selected electrosurgical instrument is to be activated with a driving electrosurgical signal with the selected waveform. In some cases, the hand controller or joystick may comprise one or more coloured LEDs near the activation button which indicates the selected waveform (e.g. a blue LED may be illuminated when a COAG waveform is selected and a yellow LED may be illuminated when CUT waveform is selected).

Thus, in addition to a surgeon being able to control the movement of an instrument 712 attached to an arm 702 via the command interface 724, when that instrument is an electrosurgical instrument the surgeon may also be able to control, from the command interface 724, when that electrosurgical instrument 712 is activated and the type of waveform of the driving electrosurgical signal.

The control unit 810 may comprise a communications module 818, one or more processors 820 and a memory 822. The communication module 818 is configured to receive control signals from the external computing device (e.g. robot control unit 718). The communications module 818 may be configured to receive the control signals from the external computing device (e.g. robot control unit 718) in any suitable manner such as, but not limited to, electrically, optically or wirelessly. For example, in some cases, the communications module 818 may be coupled to a wired communication network, such as, but not limited to, an Ethernet network, over which the communications module 818 receives the control signals from the external computing device (e.g. robot control unit 718). In other cases, the communications module 818 may be coupled to a wireless communication network, such as, but not limited to, a Wi-Fi™ network or a NFC (Near Field Communication) network, over which the communications module 818 receives the control signals from the external computing device (e.g. robot control unit 718).

In some cases, in addition to being able to receive the control signals from the external computing device (e.g. robot control unit 718) the communications module 618 may also be able to transmit data or information to the external computing device (e.g. robot control unit 718). For example, as described in more detail below, the electrosurgical connection unit 703 may also comprise an impedance measurement unit which is configured to measure the impedance across the activation switch units 806, 808 and information related to the detected impedance(s) may be transmitted to the external computing device (e.g. robot control unit 718) via the communications module 818. Where the communications module 818 can receive information from, and transmit information to, the external computing device (e.g. robot control unit 718) the communications module 818 may be described as a transceiver.

The memory 822 is configured to store computer-executable instructions that when executed by the one or more processors 820 cause the one or more processors 820 to perform the functions described herein. Specifically, the one or more processors 820 are configured (by the computer-executable instructions) to analyse any control signal received by the communications module 818 and activate one or more of the activation switches based on the analysis. The control signals are configured to indicate to the one or more processors 820 when an electrosurgical instrument is to be activated by a driving electrosurgical signal and the waveform of the driving electrosurgical signal. Both the activation information and the waveform information may be included in a single control signal or the activation information and the waveform information may be included in different control signals (e.g. there may be a control signal that indicates that the electrosurgical instrument is to be activated and a different control signal that indicates the waveform of the driving electrosurgical signal). The control signals may take any suitable form that is understood by the one or more processors 820. In some cases, as described in more detail below, the control signals may be tokens.

The one or more processors 820 are configured to analyse any control signal, or set of control signals, received by the communications module 818 to determine whether the electrosurgical instrument attached to the arm is to be activated and if the electrosurgical instrument attached to the arm is to be activated the desired waveform of the driving electrosurgical signal. In response to determining from a received control signal, or set of control signals, that the electrosurgical instrument is to be activated by a driving electrosurgical signal with a particular waveform the one or more processors 820 may be configured to activate the activation switch unit 806, 808 that will cause an activation signal to be transmitted to the electrosurgical generator 726 that indicates that the electrosurgical instrument is to be activated by a driving electrosurgical signal having that particular waveform.

For example, where there are two activation switch units 806, 808 and one activation switch unit 806 is configured to cause a first activation signal to be transmitted to the electrosurgical generator which indicates that the electrosurgical instrument is to be activated by a driving electrosurgical signal with a first waveform (e.g. CUT waveform), and the other activation switch unit 808 is configured to cause a second activation signal to be transmitted to the electrosurgical generator which indicates that the electrosurgical instrument is to be activated by a driving electrosurgical signal with a second waveform (e.g. COAG waveform), if the one or more processors 820 determine from a received control signal, or set of control signals, that the electrosurgical instrument attached to the arm is to be activated by a driving electrosurgical signal with the first waveform (e.g. CUT waveform) the one or more processors may be configured to activate the first activation switch unit 806, and if the one or more processors 820 determine from a received control signal, or set of control signals, that the electrosurgical instrument is to be activated by a driving electrosurgical signal with the second waveform (e.g. COAG waveform) the one or more processors 820 may be configured to activate the second activation switch unit 808.

In some cases, the one or more processors 820 may be configured to activate a particular activation switch unit 806, 808 by outputting one or more signals that cause all the switches 807, 809 of that activation switch unit 806, 809 to be in a closed position. An example method for processing control signals received from an external computing device, which may be implemented by the one or more processors 820, is described below with respect to FIG. 12.

In this example, a separate return electrode 824 is directly connected to the electrosurgical generator 726 via a separate cable 826.

Figure 9:
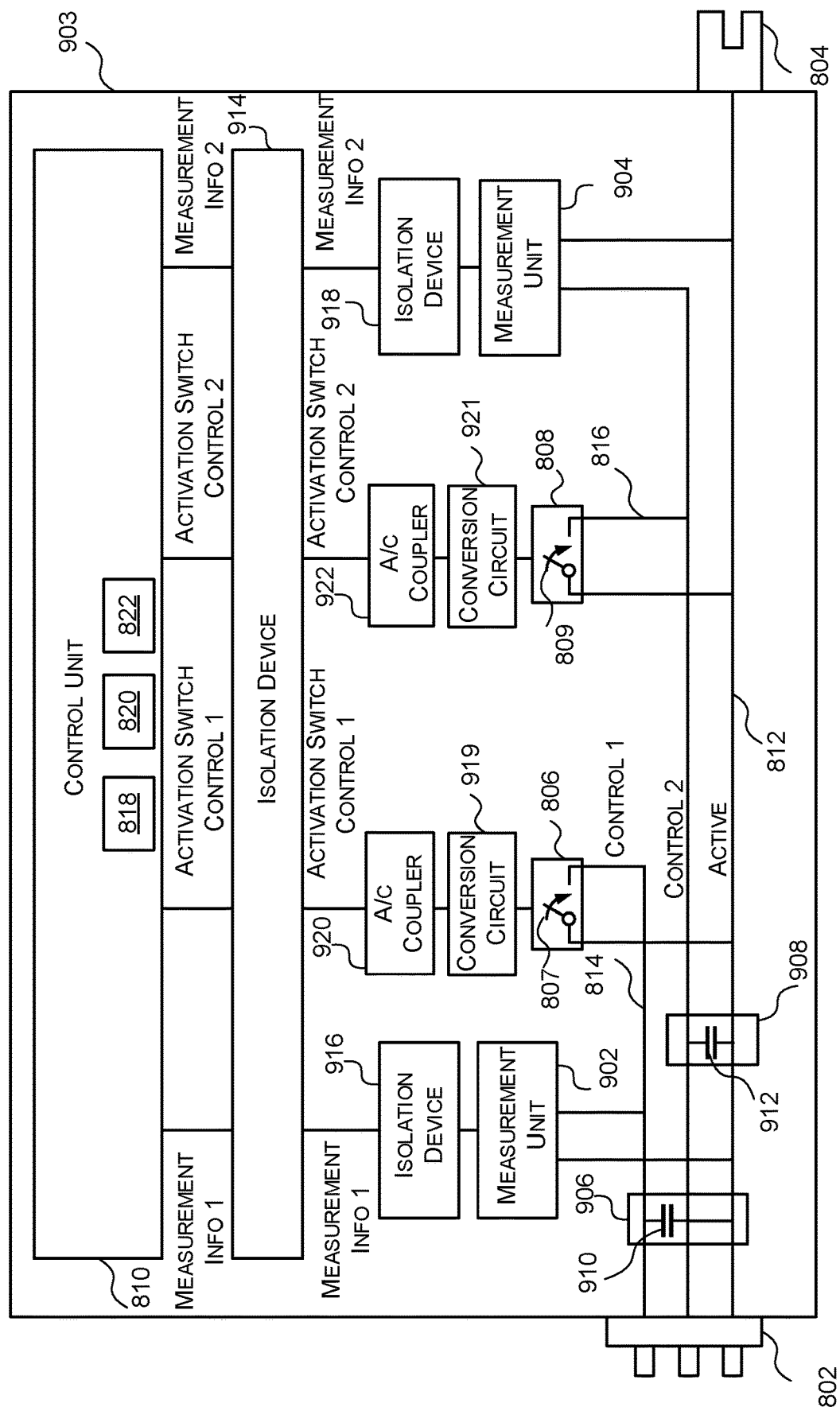
FIG. 9 is a block diagram of a second example electrosurgical connection unit for a monopolar electrosurgical instrument.

Reference is now made to FIG. 9 which illustrates a second example electrosurgical connection unit 903 for connecting a monopolar electrosurgical instrument to an electrosurgical generator 726. The example electrosurgical connection unit 903 of FIG. 9 is the same as the electrosurgical connection unit 703 of FIG. 8 except the electrosurgical connection unit 903 includes one or more further optional components.

As described above with respect to FIG. 8, it could be quite dangerous if an activation switch unit 806, 808 of the electrosurgical connection unit 903 failed such that it was stuck in an activated state (i.e. the switches 807, 809 of the activation switch unit 806, 808 are stuck in a closed position) because this would allow an activation signal to be inadvertently transmitted to the electrosurgical generator causing a driving electrosurgical signal to be inadvertently sent to an electrosurgical instrument attached to the electrosurgical connection unit 903. As a result, the electrosurgical connection unit may comprise one or more measurement units 902, 904 that are configured to measure a parameter of one or more activation switch units 806, 808 and transmit measurement information to the control unit 810 which can be used to determine whether the activation switch unit 806, 808 is working properly.

In some examples, each measurement unit 902, 904 may be an impedance measurement unit configured to measure the impedance across one or more activation switch units 806, 808. In these cases, the impedance measurement unit may be electrically coupled to both the active wire and the control wire of the relevant activation switch unit 806, 808 to measure the impedance between them. As is known to those of skill in the art, the impedance between two points of a circuit may be determined, for example, by applying a current or voltage at one point and measuring the current or voltage at the other point. However, in other examples, the measurement unit(s) may be configured to measure another parameter of the activation switch units 806, 808, such as voltage or current.

In some cases, the one or more processors 820 may be configured to control the operation of the measurement units 902, 904. For example, the one or more processors 820 may be configured to periodically place an activation switch unit 806, 808 in a deactivated state (i.e. a state in which the switches of the activation switch unit are in the open position) when the electrosurgical generator is inactive (i.e. is not outputting a driving electrosurgical signal) and then cause the measurement unit to measure the desired parameter (e.g. impedance). In these cases, when the system is started up an initialisation test may be performed to determine a benchmark measurement for the parameter (e.g. impedance) when the activation switch unit is in the deactivated state. This benchmark can then be compared against the measured parameter to determine if any of the switches is erroneously in the closed position.

In addition, or alternatively, the one or more processors may be configured to periodically place an activation switch unit 806, 808 in an activated state (i.e. a state in which the switches of the activation switch unit are in the closed position) when the electrosurgical generator is inactive (i.e. not outputting a driving electrosurgical signal) and then cause the measurement unit 902, 904 to measure the desired parameter (e.g. impedance). This measurement can be used to determine if the electrosurgical generator is active when an activation signal has not been transmitted to the electrosurgical generator.

In some cases, there may be one measurement unit 902, 904 per activation switch unit 806, 808. For example, in FIG. 9 the electrosurgical connection unit 903 comprises a first measurement unit 902 that is configured to measure a parameter (e.g. impedance) of the first activation switch unit 806 and a second measurement unit 904 that is configured to measure a parameter (e.g. impedance) of the second activation switch unit 808. In other cases, such as where the activation switch units 806, 808 comprise two or more switches in series, there may be one measurement unit 902, 904 per switch. For example, where each activation switch unit 806, 808 comprises two switches in series the electrosurgical connection unit 903 may comprise four measurement units—a first measurement unit that measures a parameter (e.g. impedance) across the first switch of the first activation switch unit 806, a second measurement unit that measures a parameter (e.g. impedance) across the second switch of the first activation switch unit 806, a third measurement unit that measures a parameter (e.g. impedance) across the first switch of the second activation switch unit 808, and a fourth measurement unit that measures a parameter (e.g. impedance) across the second switch of the second activation switch unit 808. However, in other cases there may be a single measurement unit that is configured to measure the parameter of multiple activation switch units 806, 808.

In some cases, the one or more processors 820 may be configured to receive the measurement information (e.g. the value of the measured parameter) from the measurement unit and analyse the received measurement information to determine whether the measurement information indicates that one or more of the activation switch units 806, 808 is/are not operating as expected and/or the electrosurgical generator is not operating as expected. For example, where the measurement unit is an impedance measurement unit, the one or more processors 820 may be configured to determine that one or more of the activation switch units is not operating as expected if an activation switch unit is expected to be in a deactivated state (i.e. the switches thereof are in an open position) yet there is no impedance across the activation switch unit. In response to determining that at least one of the activation switch units 806, 808 is not operating as expected or the electrosurgical generator is not operating as expected the one or more processors 820 may be configured to send an error notification to the external computing device (e.g. robot control unit 718) via the communications module 818.

In other cases, the one or more processors 820 may be configured to simply receive the measurement information from the measurement unit(s) 902, 904 and transmit the measurement information to the external computing device (or another computing device), via the communications module 818, for further analysis and processing.

Figure 3:
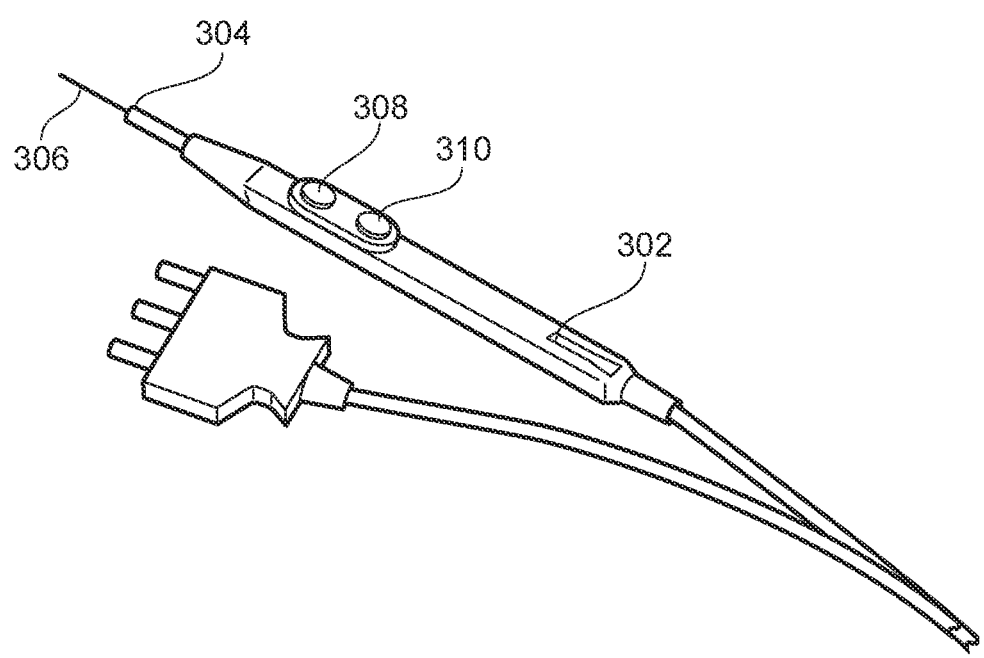
FIG. 3 is a schematic diagram of an example monopolar electrosurgical instrument with two activation buttons.
Figure 5:
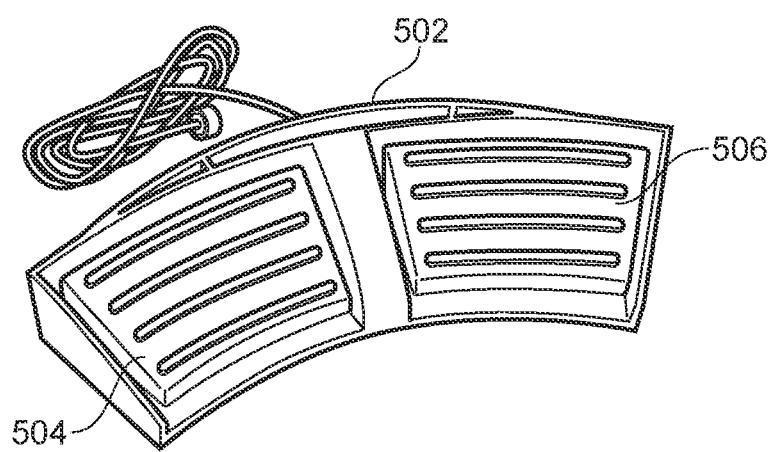
FIG. 5 is a schematic diagram of an example foot pedal system that can be used to control an electrosurgical generator.

In some cases, the control logic 728 of the electrosurgical generator 726 may be configured to detect an activation signal on a control line by measuring the impedance on the line. The control logic 728 may also be able to detect a fault or failure based on the measured impedance. In existing manual, as opposed to, robotic electrosurgical systems, such as those described above with respect to FIGS. 3-6, wherein an electrosurgical generator 726 is controlled by controls on an electrosurgical instrument or a foot pedal system, the wires in the cables connecting the electrosurgical generator to the electrosurgical instrument (FIGS. 3-4), or foot pedal system (FIGS. 5-6) typically present a significant capacitance to the electrosurgical generator 726 and the control logic 728 is configured to detect an activation signal and identify a fault condition based on that amount of capacitance on the line. In the robotic electrosurgical systems described herein wherein the electrosurgical generator 726 is controlled by an electrosurgical connection unit the wires in the cables connecting the electrosurgical generator to the electrosurgical connection unit may present a different amount of capacitance to the electrosurgical generator 726 compared to the wires in the cables used in manual electrosurgical systems. In some examples, they may present less capacitance and in other examples, they may present more capacitance. For example, in some cases, the wires in the cables used in the robotic electrosurgical systems described herein may be shorter than the wires in the cables used in manual electrosurgical systems, and thus have less capacitance than the wires in the cables used in manual electrosurgical systems.

In these cases, to ensure that the electrosurgical generator 726 can correctly detect activation signals and to prevent the electrosurgical generator 726 from erroneously detecting a fault condition on the control line, the electrosurgical connection unit 903 may comprise one or more capacitance emulation units 906, 908 each connected across one of the control wires 814, 816 and the active wire 812. Each capacitance emulation unit 906, 908 comprises one or more capacitors 910, 912 and/or one or more other capacitive components that are configured to emulate the capacitance of the corresponding wire in the cables used in manual electrosurgical system. For example, in FIG. 9, there is a first capacitance emulation unit 906 that comprises a single capacitor 910 across the first control wire 814 and the active wire 812; and a second capacitance emulation unit 908 that comprises a single capacitor 912 across the second control wire 816 and the active wire 812. The total capacitance presented by each capacitance emulation unit 906, 908 may be based on the difference between the capacitance presented by the wires in the cables used to connect the electrosurgical connection unit 903 to the electrosurgical generator 726 and the capacitance expected by the electrosurgical generator 726. It will be evident to a person of skill in the art that this is an example only and that the capacitance emulation units 906, 908 may take any suitable form that allows them to add or subtract capacitance from a control line.

It may be advantageous to isolate the control unit 810 from the active wire 812 so that the high-powered driving electrosurgical signal carried thereon does not cause damage to the one or more processors 820, memory 822 and/or communications module 818 thereof. Specifically, it may be beneficial to pass any wire connected to the control unit 810 and the active wire 812 (directly or indirectly), such as the wires used to transmit signals to the activation switch units 806, 808 to cause activation thereof, through an isolation barrier. The activation switch units 806, 808 themselves provide one isolation barrier for the control unit 810. However, in some cases this may not be sufficient to ensure that the control unit 810 is protected from the high power driving electrosurgical signals.

Accordingly, in some cases, the electrosurgical connection unit 903 may also comprise an isolation device 914 that establishes an isolation barrier between the control unit 810 and the active wire 812. In these cases, any wire connected to the control unit 810 and the active wire 812, such as the wires used to transmit signals to the activation switch units to cause activation thereof, are connected to the isolation device 914 and the data transmitted thereon is transferred to a corresponding wire connected (directly or indirectly) to the activation switch unit 806, 808 and vice versa in a manner that ensures that any high powered signal transmitted or carried on the wire connected to the activation switch unit is not transmitted or carried on the wire connected to the control unit 810. The isolation device 914 may be any suitable isolation device such as a digital isolator or an opto-isolator. As is known to those of skill in the art, digital isolators use semiconductor process technology to create either transformers or capacitors to transfer electrical signals between two isolated circuits, whereas opto-isolators transfer electrical signals between two isolated circuits using light.

Where the electrosurgical connection unit 903 also comprises one or more measurement units 902, 904, as described above, which transmit measurement information to the control unit 810, the wire on which the measurement information is transmitted from the measurement unit 902, 904 may be connected to the isolation device 914 and the information carried thereon may be transferred, by the isolation device 914, to a corresponding wire connected (directly or indirectly) to the control unit 810 in such a manner that any high powered signal carried or transmitted on the wire connected to the measurement unit 902, 904 is not carried or transmitted on the wire connected (directly or indirectly) to the control unit 810.

In some cases, where there is at least one measurement unit 902, 904 the isolation device 914 may not provide sufficient protection for the control unit 810. Accordingly, the electrosurgical connection unit 903 may further comprise one or more additional isolation devices 916, 918 between the measurement units 902, 904 and the control unit 810 to provide double isolation for the measurement information signals, like the double isolation that is provided for the control signal by the activation switch units 806, 808 and the isolation device 914. In some cases, there may be an additional isolation device 916, 918 that is situated between each measurement unit 902, 904 and the isolation device 914. For example, in the electrosurgical connection unit 903 of FIG. 9 there is a first isolation device 916 that is situated between the first measurement unit 902 and the isolation device 914, and a second isolation device 918 that is situated between the second measurement unit 904 and the isolation device 914. In some cases, one or more of the additional isolation devices may be an opto-isolator, which may also be referred to as an optocoupler, photocoupler, or optical isolator. As is known to those of skill in the art, an opto-isolator, in contrast to a digital isolator, transfers electrical signals between two isolated circuits by using light.

In some cases, the signal output by the control unit 810 to control, or activate, an activation switch unit 806, 808 is an A/C (alternating current) or oscillating signal. In some examples the control unit 810 is configured to output a 500 Hz square wave. However, it will be evident to a person of skill in the art that this is an example only. In these cases, the electrosurgical connection unit 903 may comprise a conversion circuit 919, 921 per activation switch unit 806, 808 that receives the A/C signal and groups the A/C pulses that form the A/C signal into a single D/C (direct current) pulse, which is used to activate the activation switch unit 806, 808. For example, the electrosurgical connection unit 903 of FIG. 9 comprises a first conversion circuit 919 that receives the activation switch control signal generated by the control unit 810 for the first activation switch unit 806 and converts that into a signal which activates the first activation switch unit 806; and a second conversion circuit 921 that receives the activation switch control signal generated by the control unit 810 for the second activation switch unit 808 and converts that into a signal which activates the second activation switch unit 808.

Each conversion circuit 919, 921 may be implemented as an envelope detector. Specifically, each conversion circuit 919, 921 may comprise a set of filters and diodes which are used to gradually charge a capacitor over a number of A/C pulses until the capacitor voltage switches the output of a comparator circuit. The comparator circuit may include an element of hysteresis to prevent the output changing rapidly as the capacitor charges and discharges small amounts between pulses. This means that a single pulse is incapable of causing an output signal to be output from the conversion circuit. In other words, use of an oscillating signal to activate the activation switch units means that an activation signal will not be transmitted to the electrosurgical generator if a spurious constant or momentary signal is received. Only a series of pulses in quick succession will cause an output signal to be output from the conversion circuit 919, 921.

Since a failure of the control unit 810 or the isolation device 914 is likely to result in an erroneous D/C signal (rather than an A/C signal) the electrosurgical connection unit 903 may comprise one or more A/C coupling circuits 920, 922 that precede one or more of the conversion circuits 919, 921 to ensure that a failure of the control unit 810 or the isolation device 914 cannot lead to inadvertent activation of the electrosurgical instrument. More specifically, the electrosurgical connection unit 903 may comprise one or more A/C coupling circuits 920, 922 to ensure that failure of the control unit 810 cannot lead to inadvertent activation of an activation switch unit 806, 808 which causes an activation signal being sent to the electrosurgical generator 726 resulting in the electrosurgical generator 726 outputting a driving electrosurgical signal which inadvertently activates an electrosurgical instrument attached to the electrosurgical connection unit 903.

Each A/C coupling circuit 920, 922 is configured to receive a signal and filter out the D/C (direct current) component of the signal and output only the A/C component of the signal. Each A/C coupling circuit 920, 922 may comprise one or more capacitors. In some examples there may be an A/C coupling circuit situated between the control unit 810 (or the isolation device 914 if there is one) and each conversion circuit 919, 921 which is configured to receive the corresponding activation switch control signal from the control unit 810 (or the isolation device 914 if there is one) and A/C couple this signal to the conversion circuit 919, 921 so that the conversion circuit 919, 921 receives an AC only signal (and any D/C component, erroneous or otherwise is removed). For example, the electrosurgical connection unit 903 shown in FIG. 9 comprises a first A/C coupling circuit 920 situated between the isolation device 914 and the first conversion circuit 919 which is configured to receive an activation switch control signal generated by the control unit 810 and output the A/C component of that signal; and a second A/C coupling circuit 922 situated between the isolation device 914 and the second conversion circuit 921 which is configured to receive an activation switch control signal generated by the control unit 810 and output the A/C component of that signal.

Figure 10:
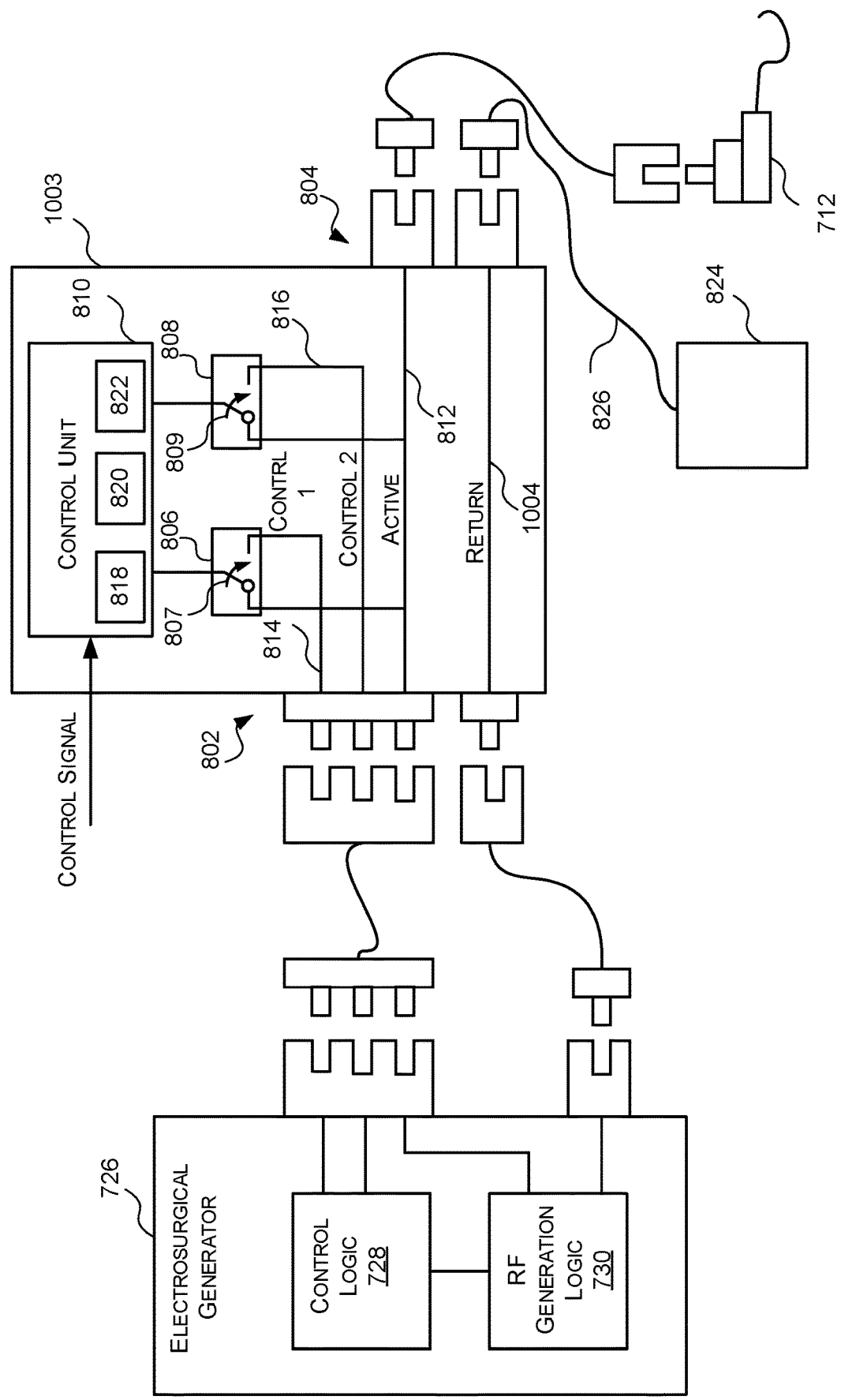
FIG. 10 is block diagram of an example electrosurgical system comprising a third example electrosurgical connection unit for a monopolar electrosurgical instrument.

Reference is now made to FIG. 10 which illustrates a third example electrosurgical connection unit 1003 for connecting a monopolar electrosurgical instrument to an electrosurgical generator 726. The example electrosurgical connection unit 1003 of FIG. 10 is the same as the electrosurgical connection unit 703 of FIG. 8 except that instead of the return electrode 330 being directly connected to the electrosurgical generator 726, the return electrode is connected to the electrosurgical connection unit 1003 and the return electrosurgical signal received from the return electrode 330 is transmitted to the electrosurgical generator via the electrosurgical connection unit 1003. In this example, the output port 804 is configured to receive the return electrosurgical signal from the return electrode 824 and transmit the received return electrosurgical signal on a return wire 1004. The return wire 1004 is also coupled to the input port 802 to allow any received return electrosurgical signal to be output on the input port 802.

As shown in FIG. 10, the output port 804 of the electrosurgical connection unit 1003 may comprise a first connector that is configured to engage a corresponding connector connected to a cable that is connected to the electrosurgical instrument, and a second connector that is configured to engage a corresponding connector connected to a cable that is connected (directly or indirectly) to the return electrode. In other examples, the output port 804 may comprise a single connector that is configured to engage a corresponding connector that is connected to two cables—one of which is connected (directly or indirectly) to the electrosurgical instrument 712, and the other of which is connected (directly or indirectly) to the return electrode 824. The output port 804 connector(s) may be female and the corresponding connectors may be male or vice versa. In many cases, the input port 802 and the output port 804 have opposite connectors to avoid electrosurgical devices from being plugged into or connected to the wrong port (i.e. to avoid an electrosurgical instrument being inadvertently plugged into the input port 802 and/or an electrosurgical generator 726 being inadvertently plugged into the output port 804). For example, in some cases the input port 802 may have male connectors(s) and the output port 804 may have female connector(s).

As shown in FIG. 10, the input port 802 of the electrosurgical connection unit 1003 may comprise a first connector that is configured to engage a corresponding connector connected to a cable that is connected (directly or indirectly) to the electrosurgical generator and is configured to carry the driving electrosurgical signal and control signals between the electrosurgical generator 726 and the electrosurgical connection unit 1003; and a second connector that is configured to engage a corresponding connector connected to a cable that is connected (directly or indirectly) to the electrosurgical generator and is configured to carry the return electrosurgical signal from the electrosurgical connection unit 1003 and the electrosurgical generator 726. In other examples, the input port 802 may comprise a single connector that is configured to engage a corresponding connector that is connected to a cable connected (directly or indirectly) to the electrosurgical generator 726. In yet other examples, the input port 802 may have any number of connectors that are configured to engage corresponding connectors to enable the driving electrosurgical signal, the control signals and the return electrosurgical signal to be transmitted between the electrosurgical generator and the electrosurgical connection unit 1003. The input port 802 connector(s) may be male and the corresponding connectors which engage the input port 802 connectors may be female or vice versa.

Figure 11:
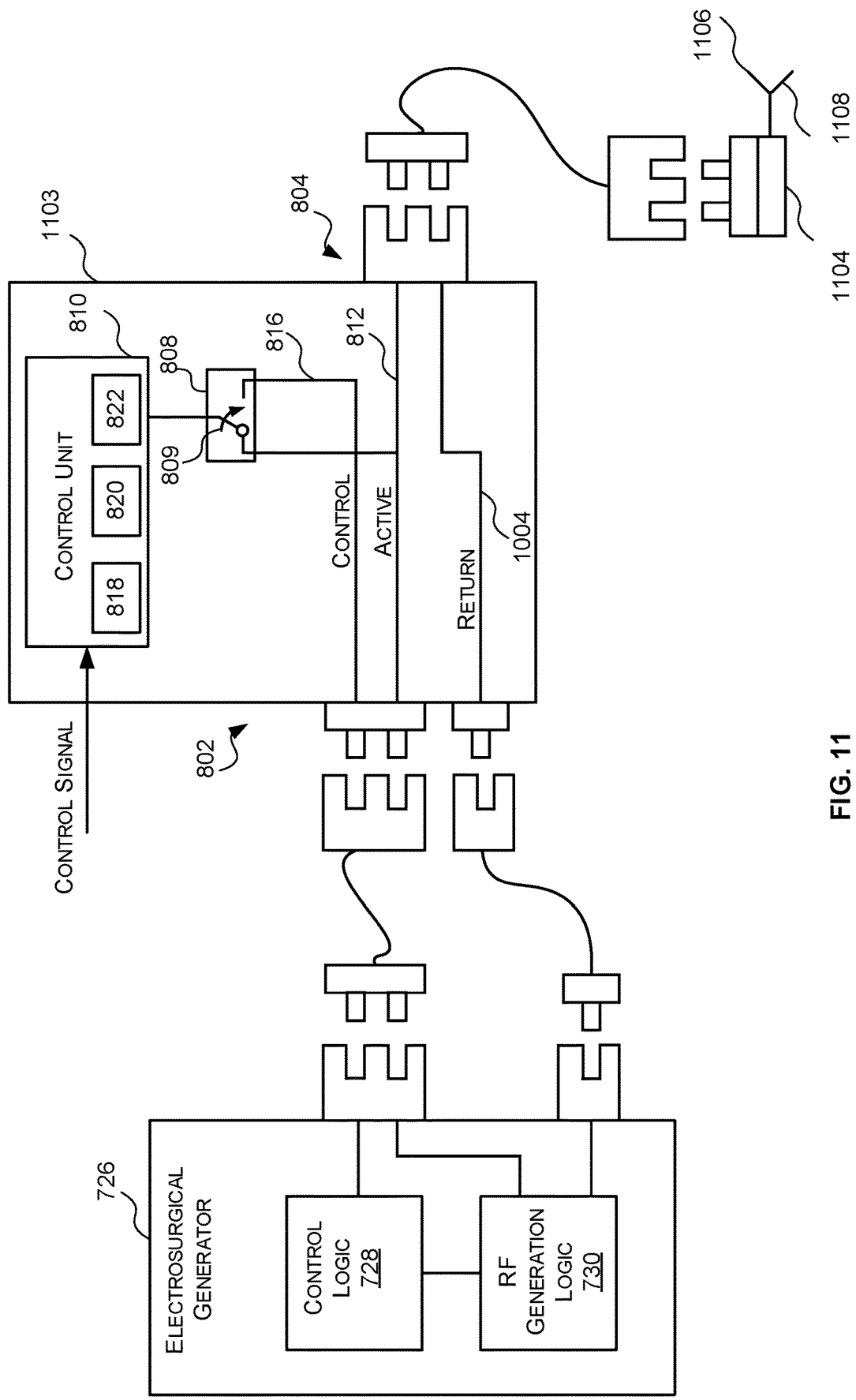
FIG. 11 is a block diagram of an example electrosurgical system comprising an example electrosurgical connection unit for a bipolar electrosurgical instrument.

Reference is now made to FIG. 11 which illustrates an example electrosurgical connection unit 1103 for connecting a bipolar electrosurgical instrument 1004 to an electrosurgical generator 726. As described above, a bipolar electrosurgical instrument comprises both an active electrode 1106 and a return electrode 1108. The active electrode 1106 is activated by a driving electrosurgical signal generated by the electrosurgical generator 726 and the return electrode 1108 receives the return electrosurgical signal which is transmitted to the electrosurgical generator 726. The active and return electrodes 1106, 1108 may be made of, or may comprise, an electrically conductive type material, such as, for example, stainless steel. Some bipolar electrosurgical instruments may not be capable of being driven by driving electrosurgical signals with at least two different preconfigured waveforms. The bipolar instrument can either be activated or not by the bipolar waveform configured on the electrosurgical generator.

Accordingly, the electrosurgical connection unit 1103 of FIG. 11 is the same as the electrosurgical connection unit 1003 of FIG. 10 where the return electrosurgical signal is received on the output port 804 and transmitted out the input port 802 via a return wire 1004 connecting the input port and the output port, except that the there is only one activation signal and thus only one control wire 816 and only one activation switch unit 808. When the activation switch unit 808 is activated is sends an activation signal to the electrosurgical generator 726 that indicates that a driving electrosurgical signal with a bipolar waveform is to be activated which, when detected by the electrosurgical generator 726 causes the electrosurgical generator 726 to output a driving electrosurgical signal with the bipolar waveform.

As described above with respect to FIG. 10, the output port 804 may comprise multiple connectors, one for each of the driving electrosurgical signal and the return electrosurgical signal, which are configured to engage corresponding connectors which are each connected to a cable that is configured to carry one of the driving electrosurgical signal and the return electrosurgical signal. However, in most cases, since the driving electrosurgical signal is provided to the electrosurgical instrument and the return electrosurgical signal is received from the electrosurgical instrument the output port 804 comprises a single connector that is configured to engage a corresponding connector which is connected to a cable that is configured to carry both the driving electrosurgical signal and the return electrosurgical signal.

Although the electrosurgical connection units 703, 903, 1003 of FIG. 8-11 were described as supporting either a bipolar electrosurgical instrument or a monopolar electrosurgical instrument, other example electrosurgical connection units may comprise components to support both monopolar electrosurgical instruments and bipolar electrosurgical instruments. Such electrosurgical connection units may comprise all the components of the electrosurgical connection unit 703, 903, or 1003 described above to support a monopolar electrosurgical instrument and all of the components of the electrosurgical connection unit 1103 of FIG. 11 to support a bipolar electrosurgical instrument. For efficiency such electrosurgical connection units may comprise a single control unit that controls all of the activation switch units (i.e. the activation switch units that control activation of a monopolar electrosurgical instrument and the activation switch units the control activation of a bipolar electrosurgical instrument). An electrosurgical instrument attached to the arm may then be dynamically connected to the monopolar components or the bipolar components depending on whether the electrosurgical instrument is a monopolar electrosurgical instrument or a bipolar electrosurgical instrument.

Any of the electrosurgical connection units 703, 903, 1003, or 1103 described above with respect to FIGS. 8, 9, 10, and 11 may comprise any combination of the optional features described above with respect to FIG. 9.

Figure 12:
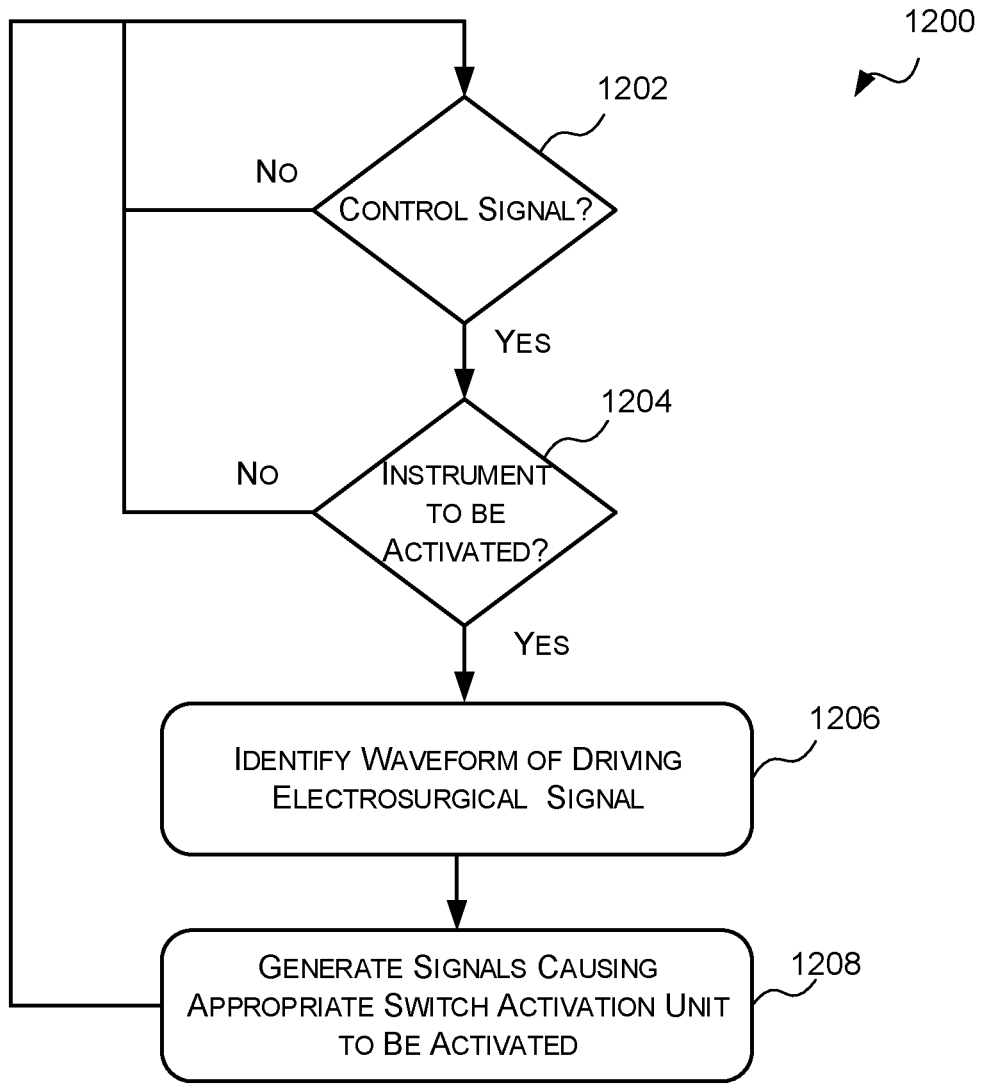
FIG. 12 is a flow diagram of an example method for selectively activating activation switch units of an electrosurgical connection unit.

Reference is now made to FIG. 12 which illustrates an example method 1200 which may be executed by the control unit 810 (e.g. the one or more processors 820 of the control unit) to selectively active the activation switch units. The method 1200 begins at block 1202 where the control unit (e.g. the one or more processors 820 of the control unit) determines whether it has received (e.g. via the communications module 818) a control signal or a set of control signals from an external computing device. If the control unit (e.g. the one or more processors 820) determines that it has received a control signal, or a set of control signals, then the method 1200 proceeds to block 1204. If, however, the control unit (e.g. the one or more processors 820) determines that is has not received a control signal or a set of control signals then the method 1200 proceeds back to block 1202.

At block 1204, the control unit 810 (e.g. the one or more processors 820) determines whether the control signal or set of controls signals indicate that an electrosurgical instrument attached to the arm is to be activated by a driving electrosurgical signal. If the control unit 810 (e.g. the one or more processors 820) determines that the control signal or set of control signals indicate that an electrosurgical instrument attached to the arm is to be activated, then the method 1200 proceeds to block 1206. If, however, the control unit 810 (e.g. the one or more processors 820) determines that the control signal or set of control signals do not indicate that the electrosurgical instrument attached to the arm is to be activated then the method 1200 proceeds back to block 1202.

At block 1206, the control unit 810 (e.g. the one or more processors 820) determines from the control signal, or set of control signals, the waveform to be used for the driving electrosurgical signal. For example, where a monopolar electrosurgical instrument can be driven by a COAG waveform or a CUT waveform the control unit 810 (e.g. the one or more processors 820) may analyse the control signal, or set of control signals, to determine which waveform is to be used for the driving electrosurgical signal. Once the control unit 810 (e.g. the one or more processors 820) has determined the waveform for the driving electrosurgical signal the method 1200 proceeds to block 1208.

At block 1208, the control unit 810 (e.g. one or more processors 820) identifies the activation switch unit to be activated to cause a driving electrosurgical signal with the determined waveform to be generated and generates one or more signals causing the identified activation switch unit to be activated (e.g. causes the switch(es) of the identified activation switch unit to be in a closed position). For example, where a monopolar electrosurgical instrument can be driven by a COAG waveform or a CUT waveform the control unit 810 determines which of the activation switch units is associated with the determined waveform and then generates one or more signals causing that activation switch unit to be activated. In particular, if it is determined that the driving electrosurgical signal is to have a CUT waveform the control unit 810 (e.g. the one or more processors 820) determines which activation switch unit is associated with a CUT waveform and then generates one or more control signals to cause that activation switch unit to be activated. This causes a cut activation signal to be sent to the electrosurgical generator, which when detected by the electrosurgical generator causes the electrosurgical generator to output a driving electrosurgical signal with a CUT waveform. The method 1200 then proceeds back to block 1202.

In some cases, the control unit 810 may be configured to output one or more control signals that cause the appropriate activation switch unit to be activated for only a predetermined period (e.g. a few milliseconds) and then the method 1200 proceeds back to block 1202 where the control unit 810 determines whether it has received a new control signal (or set of control signals) indicating that the activation switch unit 806, 808 should continue to be activated. In this way the control unit 810 only causes the appropriate activation switch unit 806, 808 to be activated while the control unit 810 continues to receive a control signal (or a set of control signals) indicating that the activation switch unit 806, 808 is to be activated. The predetermined period is generally quite short (e.g. a few milliseconds) to allow the control unit 810 to respond quickly to a change from activation to deactivation (or vice versa) and from one type of activation to another (e.g. from a driving electrosurgical signal with a first waveform to a driving electrosurgical signal with a second waveform).

In some cases, the control unit 810 may be configured to implement the method 1200 of FIG. 12 using a token-based approach to verify the latency between the control unit 810 and the external computing device (e.g. robot control unit 718) generating the control signal(s) so that stale control signals can be ignored. In the token-based approach the control unit 810 is configured to generate a new token on a periodic basis. For example, the control unit 810 may be configured to generate a new token at a frequency of 1 kHz. The token comprises information that indicates the time at which the token was generated. For example, the control unit 810 may be configured to update a rolling counter (e.g. a 16-bit counter) each period and include the latest counter value in the token for that period. The token may also comprise information that uniquely identifies the electrosurgical connection unit to which the control unit 810 belongs (e.g. an electrosurgical connection unit identifier (ID)).

In some cases, the token may also comprise validation information which indicates whether the token is valid (e.g. has not been corrupted). For example, the token may also comprise a CRC (cyclic redundancy check) value based on some or all the information (e.g. fields) in the token. In some cases, each token may comprise an 8-bit CRC value.

Once the token has been generated, the control unit 810 transmits, directly or indirectly, (e.g. via the communication module 818) the generated token to the external computing device (e.g. robot control unit 718) that generates the control signal for the electrosurgical connection unit.

The external computing device (e.g. robot control unit 718) receives the token and if the external computing device receives information indicating that the electrosurgical instrument attached to the electrosurgical connection unit identified in the token is to be activated by a driving electrosurgical signal with a particular waveform the token is modified to indicate the particular waveform to be generated and the updated token is transmitted back to the control unit 810. For example, as described above the command interface may comprise a display and one or more hand controllers or joysticks. The surgeon, or other user, may be able to select, via a graphical user interface displayed on the display, the waveform to be generated and the electrosurgical instrument to be activated. The surgeon, or other user, may then be able to indicate that the selected electrosurgical instrument is to be activated with the selected waveform by pressing an electrosurgical activation button on the hand controller or joystick. In these examples, when the user presses the electrosurgical activation button the token related to the electrosurgical connection unit to which the selected arm is attached is updated with information indicating the selected waveform. Where the token includes validation information the validation information (e.g. CRC value) may be updated to reflect the waveform information added to the token.

Where, for example, the electrosurgical generator supports three different waveforms (e.g. a monopolar COAG waveform, a monopolar CUT waveform, and a bipolar waveform) the token may comprise a two-bit waveform field which indicates the selected waveform. For example, a "01" in the waveform field may indicate a monopolar COAG waveform, a "10" in the waveform field may indicate a monopolar CUT waveform, and a "11" may indicate a bipolar waveform.

In some cases, the external computing device (e.g. robot control unit 718), or one or more other devices which receive the token prior to the electrosurgical connection unit, may be configured to negate the token if one or more conditions for activating the selected electrosurgical instrument with the selected waveform are not met (or, alternatively, when a fault condition is detected). For example, the external computing device (e.g. robot control unit 718) and/or one or more other devices may be configured to negate a token if and when any of the following conditions are detected: (i) the user is not currently controlling an arm that is connected to an electrosurgical instrument (e.g. the hand controller or joystick on which the activation button was pressed is not actively connected to an arm that is connected to an electrosurgical instrument); (ii) the validation information indicates the token is invalid (e.g. a CRC check fails); (iii) the electrosurgical instrument attached to the selected arm does not support the selected waveform; (iv) the electrosurgical instrument, the arm or the electrosurgical connection unit is in a fault mode; and (v) the communications network (e.g. Ethernet network) over which the external computing device and the electrosurgical connection unit communicate is faulty. It will be evident to a person of skill in the art that these are examples only and that other conditions or fault states may cause a token to be negated. In some cases, negating the token may comprise setting all fields of the token (including the validation field where there is one) to zero which may be referred to as a zeroed token. In some cases, a negated token is not passed on to the electrosurgical connection unit.

When the modified token is received at the electrosurgical connection unit the electrosurgical connection unit is deemed to have received a control signal (block 1202 of method 1200). The control unit 810 then determines whether the modified token indicates that an electrosurgical instrument attached to the electrosurgical connection unit is to be activated (block 1204 of method 1200). The control unit 810 may determine that the modified token indicates that an electrosurgical instrument attached to the electrosurgical connection unit is to be activated (i) if the information in the token identifying the electrosurgical connection unit that generated the token matches the identifying information for the current electrosurgical connection unit; and (ii) if the information indicating when the token was generated (counter information) indicates that less than a predetermined amount of time has elapsed since the token was generated. In some cases, the control unit 810 may determine that less than a predetermined amount of time has elapsed since the token was generated by comparing the counter information in the token to the current value of the counter (e.g. by computing the difference) and determining whether the difference exceeds a threshold. In some cases, the threshold may be set so that the predetermined time is only a few milliseconds.

Where the token comprises validation information (e.g. a CRC value) the control unit 810 may only determine that the token indicates that an electrosurgical instrument attached to the electrosurgical connection unit is to be activated if the above conditions are met and the validation information indicates that the token is valid (e.g. a CRC check passes).

If the control unit 810 determines that the token indicates that an electrosurgical instrument attached to the electrosurgical connection unit is to be activated then the control unit 810 analyses the token to identify the desired waveform for the driving electrosurgical signal (block 1206 of method 1200).

Once the control unit 810 identifies the desired waveform for the driving electrosurgical signal the control unit 810 identifies the switch activation unit 806, 808 associated with the desired waveform and generates one or more signals causing the identified activation switch unit 806, 808 to be activated (e.g. causes the switches 807, 809 of the identified activation switch unit 806, 808 to be in a closed position) (block 208 of method 1200). For example, as described above, the control unit 810 may generate an oscillating signal (e.g. a square wave) for a predetermined period that causes the identified activation switch unit to be activated.

Figure 13:
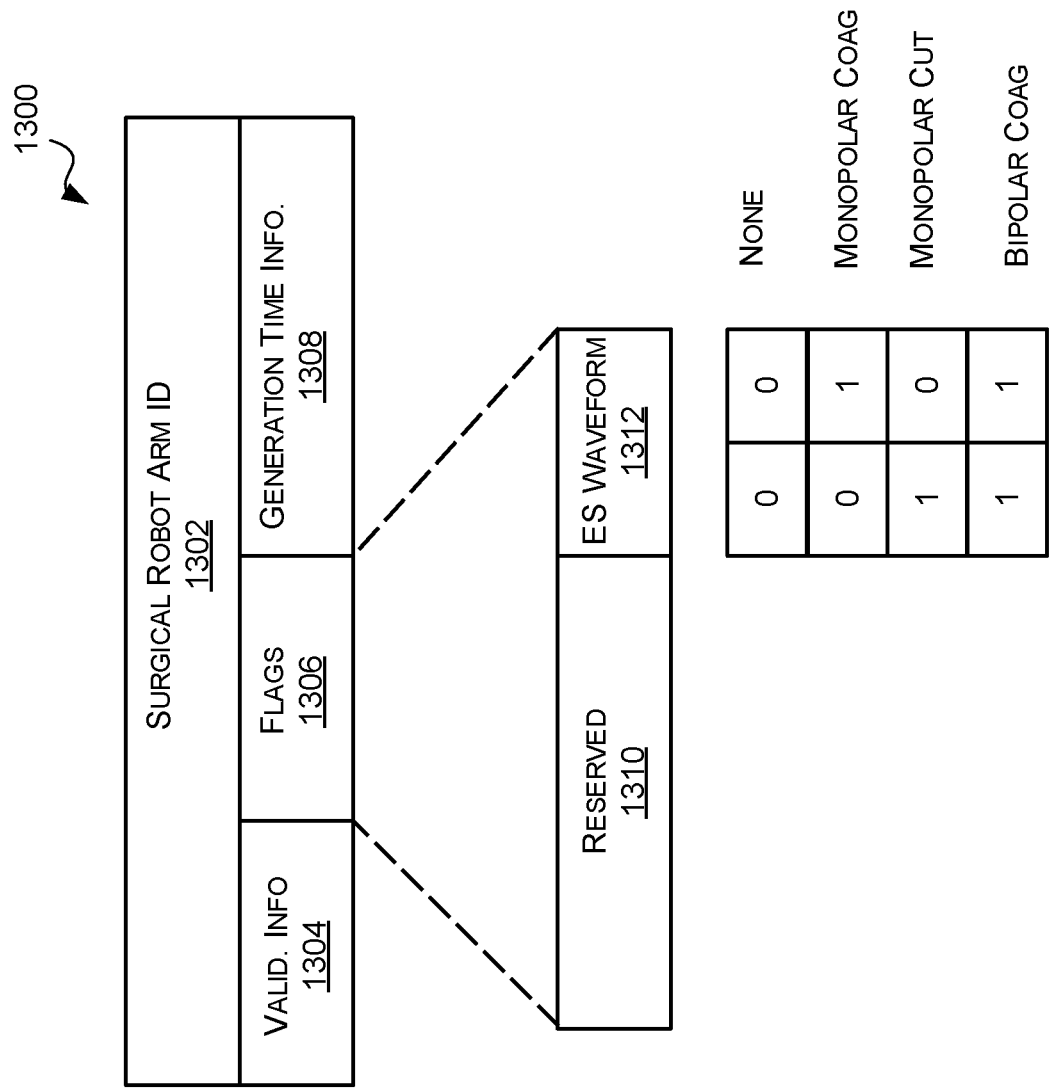
FIG. 13 is a schematic diagram illustrating an example format of a token for use in activating an electrosurgical instrument.

Reference is now made to FIG. 13 which illustrates an example format for such a token 1300, which may be referred to as an electrosurgery token. In the example of FIG. 13, the token 1300 comprises four fields—a surgical robot arm identifier (ID) field 1302, a validation information field 1304, a flags field 1306, and a generation time information field 1308. In one example, the token 1302 may be a 64-bit token wherein the surgical robot arm ID field 1304 is 32 bits, the valid information field is 8 bits, the flags field 1306 is 8 bits and the generation time information field 1308 is 16 bits. However, it will be evident to a person of skill in the art that this is an example only and that other tokens with additional or alternative fields may be used and the token and the fields therein may have a different number of bits.

The surgical robot arm ID field 1302 is used to store information that uniquely identifies the surgical robot arm associated with the control unit 810 which generated the token. As described above, information that uniquely identifies the surgical robot arm may comprise information that uniquely identifies the electrosurgical connection unit to which the control unit 810 belongs. In some cases, the control unit 810 may comprise a unique serial number and the information uniquely identifying the surgical robot arm may be a serial number of the control unit 810.

The validation information field 1304 comprises information that indicates whether the token is valid (e.g. has not been corrupted). In some cases, the information indicating the token is valid may comprise an error detection code. For example, as described above, in some cases the validation information may comprise a CRC value or code based on some or all of the information (e.g. fields) in the token. As it could be disastrous to activate an electrosurgical instrument based on a corrupt token (e.g. it could cause the electrosurgical instrument to be activated by the wrong waveform), using a CRC value to validate the token may provide an extra safety measure as it means that if any bit in the entire token is corrupted the whole token will be invalid.

The flags field 1306 may be divided into two sub-fields—a reserved field 1310 and an electrosurgical waveform field 1312, which may also be referred to as an electrosurgical mode field. The electrosurgical waveform field is used to indicate the waveform of the driving electrosurgical signal. In one example, the electrosurgical waveform field 1312 may be two-bits and a '00' in the electrosurgical waveform field 1312 may indicate no waveform has been selected, a '01' in the electrosurgical waveform field 1312 may indicate that a monopolar COAG waveform is to be activated, a '10' in the electrosurgical waveform field 1312 may indicate that a monopolar CUT waveform is to be activated, and a '11' in the electrosurgical waveform field 1312 may indicate that a bipolar COAG waveform is to be activated. It will be evident to a person of skill in the art that this is an example only and in other examples the electrosurgical waveform may have more or fewer bits based on the number of different waveforms supported by the electrosurgical generators used to drive the electrosurgical instrument(s). Specifically, to support more waveforms the electrosurgical waveform field 1312 may comprise more bits. Examples of additional waveforms that may be supported include, but are not limited to, a bipolar CUT waveform and a BLEND waveform (described above).

In some cases, the token generated by the control unit 810 may comprise information in the electrosurgical waveform field 1312 that indicates that no waveform has been selected (e.g. it may be set to '00') and only if the control unit 810 receives a modified version of the token in which the electrosurgical waveform field 1312 indicates a waveform has been selected (e.g. it is non-zero) will the control unit 810 activate an activation switch unit. It will be evident to a person of skill in the art that this is an example only and that there may be a different number and/or type of supported waveforms and/or the waveforms may be indicated using a different combination of 1's and 0's.

The generation time information field 1308 comprises information indicating the time at which the token was generated. As described above, in some cases the control unit 810 may be configured to update a rolling counter on a periodic basis and the information indicating the time at which the token was generated may comprise the value of the counter at the time the token is generated.

The token-based approach described above means that the latency can be verified end to end without reference to more complicated clock synchronisation or link-specific latency detection methods. It also controls the risk that a computer system between the external computing device and the electrosurgical connection unit might get stuck repeating the same stale activation state and renders such behaviour harmless.

Figure 14:
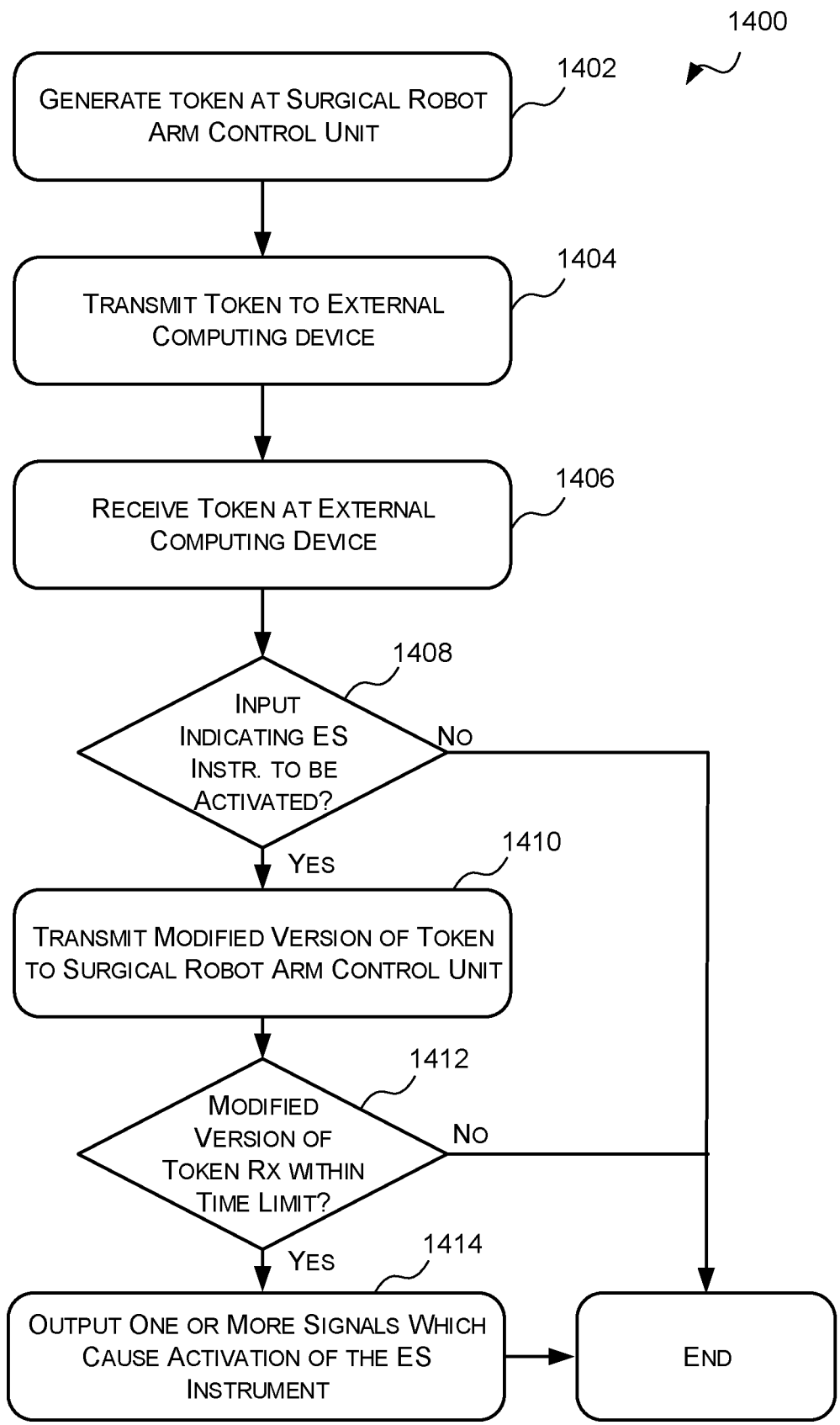
FIG. 14 is a flow diagram of an example token-based method for remotely activating an electrosurgical instrument attached to a surgical robot arm.

Reference is now made to FIG. 14 which illustrates an example token-based method 1400 for remotely activating an electrosurgical instrument 712 attached to a surgical robot arm 702. The method 1400 begins at block 1402 where the control unit 810 associated with the surgical robot arm, which may be referred to herein as the surgical robot arm control unit, generates a token comprising information indicating a time at which the token was generated. In some cases, the control unit 810 may be configured to periodically (e.g. at a frequency of 1 kHz) increment, or modify, a rolling counter (e.g. a 16-bit counter) and the information in a token indicating the time at which the token was generated may comprise the value of the counter at the time the token was generated. In some cases, the token may also comprise information uniquely identifying the surgical robot arm.

In some cases, the token may further comprise validation information that indicates whether the token is valid. For example, as described above, the token may comprise an error detection code, such as, but not limited to a cycle redundancy check (CRC) code, that is based on some or all of the information (e.g. fields) in the token.

At block 1404, the surgical robot control unit 810 transmits the token, directly or indirectly (e.g. via the communication module 818) to an external computing device (e.g. robot control unit 718). The token may be transmitted to the external computing device using any suitable communication means, such as those described above in relation to the communication module 818. The method 1400 then proceeds to block 1406.

At block 1406, the token is received at the external computing device (e.g. robot control unit 718). The method 1400 then proceeds to block 1408. In some cases, the method 1400 may only proceed to block 1408 if it is determined that the token relates to a surgical robot arm that is currently being controlled by a user; if it is determined (e.g. from the validation information) that the token is valid; and/or if it is determined that the surgical robot arm to which the token relates currently has an electrosurgical instrument attached thereto. If one or more of these conditions are determined not to be true then the token may be discarded and/or invalidated (e.g. zeroed) and the method 1400 may end.

At block 1408, the external computing device determines whether it has received input indicating that the electrosurgical instrument 712 is to be activated. For example, as described above, the command interface may comprise a display and one or more devices, such as, but limited to hand controllers or joysticks, that are used to control the surgical robot arm. The surgeon or other user may be able to indicate that a selected electrosurgical instrument (e.g. the electrosurgical instrument attached to the surgical robot arm currently being controlled by the device) is to be activated by selecting or otherwise activating an input on the device, such as, but not limited to an electrosurgical activation button. In these cases, when the user activates the input (e.g. electrosurgical activation button) the external computing device (e.g. robot control unit 718) may receive input that the selected electrosurgical instrument is to be activated. If the external computing device has received input indicating that the electrosurgical instrument 712 is to be activated, the method 1400 proceeds to block 1410. Otherwise the method 1400 ends.

At block 1410, in response to receiving input at the external computing device (e.g. robot control unit 718) indicating that the electrosurgical instrument 712 is to be activated, a modified version of the received token, which may also be referred to as an updated token, is transmitted to the surgical robot control unit 810. The modified version of the token indicates that the electrosurgical instrument 712 is to be activated.

In some cases, the modified version of the token may be generated by adding information to the token indicating the desired waveform to activate the electrosurgical instrument. For example, the initial token generated by the surgical robot arm control unit 810 may indicate that no waveform has been selected (e.g. the electrosurgical waveform field 1312 may be '00') and by modifying the token to indicate a particular waveform the modified version of the token indicates that the electrosurgical instrument is to be activated As described above, the desired waveform may be any waveform supported by the system (e.g. capable of being generated by the electrosurgical generators used to drive the electrosurgical instrument(s)). Examples of waveforms that may be supported by the system include, but are not limited to, monopolar coagulation (COAG) waveform, monopolar cut (CUT) waveform, bipolar coagulation (COAG) waveform, bipolar cut (CUT) waveform, and one or more BLEND waveforms.

In some cases, the surgeon, or other user, may be able to select, via a graphical user interface displayed on the display of the user interface the waveform of the driving electrosurgical signal and when the external computing devices receives an indication that the surgical instrument is to be activated then the token is modified to indicate the waveform pre-selected by the user is the desired waveform. Where the modified version of the token comprises information indicting the waveform of the driving electrosurgical signal, prior to transmitting the modified version of the token, the external computing device (e.g. robot control unit 710) may determine if the electrosurgical instrument to be activated supports the waveform indicated in the modified version of the token. In these cases, the external computing device may only transmit the modified version of the token to the surgical robot arm control unit if it is determined that the electrosurgical instrument supports the indicated waveform.

In some cases, where the token has validation information, modifying the token to generate the modified version of the token many further comprise modifying the validation information (e.g. CRC code) in the token to reflect the changes to the token (e.g. waveform information etc.). In this way the modified version of the token may comprise updated validation information (e.g. CRC code).

In some cases, prior to transmitting the modified version of the token to the surgical robot arm control unit, the external computing device (e.g. robot control unit 718) may determine, from the validation information in the modified version of the token, whether the modified version of the token is valid. If the modified version of the token is not valid then it may have been corrupted and it is not safe to send it to the surgical robot arm control unit. Accordingly, in these cases, the external computing device may only transmit the modified version of the token to the surgical robot arm control unit if it is determined that the modified version of the token is valid.

In some cases, prior to transmitting the modified version of the token to the surgical robot arm control unit, the external computing device (e.g. robot control unit 718) may determine whether the surgical robot arm is currently being controlled by a user. If the surgical robot arm is not currently being controlled by a user then it may not be safe to activate an electrosurgical instrument attached thereto. In these cases, the external computing device may only transmit the modified version of the token to the surgical robot arm control unit if it is determined that the surgical robot arm to which the surgical instrument is attached is currently being controlled by a user.

In some cases, the external computing device may receive input that the electrosurgical instrument is to be activated when a user activates an input on a device used to control the surgical robot arm. In these cases, the external computing device may only transmit the modified version of the token to the surgical robot arm control unit if the input is received when the device is being used by a user. Where the device is a hand controller, joystick or the like the device may comprise a sensor to detect when the device is being grasped or held by a user and the external computing device may determine that the device is being used by the user if the sensor had detected that the device is being grasped or held by the user.

Once the modified version of the token has been transmitted to the surgical robot arm control unit, the method 1400 proceeds to block 1412.

At block 1412, the surgical robot arm control unit 810 determines whether the modified version of the token has been received within a threshold amount of time from when the token was generated. Where, as described above, the control unit 810 periodically updates a counter and the information in a token that indicates the time at which the token was generated is the value of the counter at the time the token was generated, the surgical robot arm control unit 810 may compare the information in the modified version of the token indicating the time at which the token was generated to the current value of the counter to determine whether the modified version of the token was received within the threshold amount of time from when the token was generated. For example, the control unit 810 may compute the difference between the counter value in the modified version of the token and the current counter value and determine that the token was received within the threshold amount of time if the difference does not exceed a threshold.

If it is determined that the modified version of the token has been received within the threshold amount of time then the method 1400 proceeds to block 1414. Otherwise, the method 1400 ends.

At block 1414, in response to the surgical robot arm control unit 810 receiving the modified version of the token within a threshold amount of time from when the token was generated, one or more signals are output that cause the electrosurgical instrument to be activated by a driving electrosurgical signal.

In some cases, where a token comprises information uniquely identifying the surgical robot arm, the surgical robot arm control unit 810 may only output the one or more signals if the modified version of the token comprises the information that uniquely identifies the surgical robot arm. In other words, in these cases, the surgical robot arm control unit 810 may only output the one or more signals if the information identifying a surgical robot arm in the modified version of the token matches the identifying information for the surgical robot arm that the control unit 810 controls.

In some cases, where a token comprises validation information, the surgical robot arm control unit 810 may, prior to outputting the one or more signals, determine, based on the validation information in the modified version of the token, whether the modified version of the token is valid. For example, the surgical robot arm may perform a CRC check on the CRC code or value in the modified version of the token to determine if the modified version of the token is valid. In these cases, the surgical robot arm control unit 810 may only output the one or more control signals if it is determined the modified version of the token is valid.

In some cases, the surgical robot arm control unit 810 may, prior to outputting of the one or more signals, determine whether the electrosurgical instrument and/or the surgical robot arm are in a suitable state for electrosurgical activation. The electrosurgical instrument and/or the surgical robot arm may be deemed not be in a suitable state for electrosurgical activation if, for example, the electrosurgical instrument and/or the surgical robot arm are in a fault state. In these cases, the surgical robot arm may be configured to only output the one or more signals if it is determined that the electrosurgical instrument and/or the surgical robot arm are in a suitable state for electrosurgical activation.

Where the modified version of the token comprises information indicating the waveform of the driving electrosurgical signal then the surgical robot arm control unit 810 may generate the one or more signals so as to cause the electrosurgical instrument to be activated by a driving electrosurgical signal with the waveform identified in the modified version of the token.

In some cases, the one or more control signals output by the surgical robot arm control unit are provided to an activation switch unit (such as the activation switch units described above), which causes activation of the activation switch unit. As described above, activation of the activation switch unit causes an activation signal to be transmitted to an electrosurgical generator. In some cases, the one or more signals output by the surgical robot arm control unit may comprises an oscillating signal, such as, but not limited to a square wave.

In some cases, the modified version of the token may be transmitted from the external computing device to the surgical robot arm control unit via one or more processing units. The one or more processing units may form part of the external computing device or may be separate and distinct from the external computing device. In these cases, any or all of these processing units may be configured to determine whether, at the time they receive the modified version of the token, that a non-electrosurgical activation state exists; and if a non-electrosurgical activation state is exists, discarding or invaliding the modified version of the token. As described above, a non-electrosurgical activate state may be any state of the modified version of the token, electrosurgical instrument, or surgical robot arm in which the modified version of the token shouldn't be used to activate the electrosurgical instrument.

Example non-electrosurgical activation states include, but are not limited to: the modified version of the token is invalid (e.g. as indicated by the validation information); the electrosurgical instrument does not support the waveform indicated in the modified version of the token; the surgical robot arm is not currently being controlled by a user; and the surgical robot arm is not in a surgical mode (i.e. a mode in which it can be used to perform surgery).

Although the control unit 810 is described as being part of an electrosurgical connection unit that activates an electrosurgical instrument by activating an activation switch unit, it will be evident to a person of skill in the art that the method may be implemented using any control unit associated with the surgical robot arm and that the electrosurgical instrument may be activated using any suitable means. For example, instead of activating an activation switch the one or more signals may be sent directly or indirectly to an electrosurgical generator which cause the electrosurgical generator to output a driving electrosurgical signal which activates the electrosurgical instrument.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein. In view of the foregoing description it will be evident to a person skilled in the art that various modifications may be made within the scope of the invention.

The invention claimed is:

1. An electrosurgical connection unit for a surgical robot arm, the electrosurgical connection unit comprising:
    an input port connectable to an electrosurgical generator, wherein when the input port is connected to the electrosurgical generator, the input port is configured to:
        output one or more activation signals to the electrosurgical generator which cause the electrosurgical generator to output a driving electrosurgical signal configured to drive an electrosurgical instrument, and
        receive the driving electrosurgical signal output by the electrosurgical generator;
    an output port connectable to the electrosurgical instrument, the output port configured to output the driving electrosurgical signal received on the input port;
    one or more activation switch units, wherein activation of an activation switch unit of the one or more activation switch units causes an activation signal to be output from the input port that indicates to the electrosurgical generator that a desired waveform is to be used to generate the driving electrosurgical signal;
    a control unit configured to selectively activate one of the one or more activation switch units in response to a control signal; and
    a measurement unit configured to measure a parameter of an activation switch unit of the one or more activation switch units and output measurement information to the control unit, the measurement information enabling a determination to be made as whether that activation switch unit of the one or more activation switch units is operating as expected.

2. The electrosurgical connection unit of claim 1, wherein the input port is coupled to an active wire for receiving the driving electrosurgical signal and one or more control wires for transmitting an activation signal, and when an activation switch unit of the one or more activation switch units is activated the active wire is connected to one of the one or more control wires to generate the activation signal.

3. The electrosurgical connection unit of claim 2, wherein each activation switch unit of the one or more activation switch units comprises one or more switches in series and one end of the series of switches is coupled to the active wire and the other end of the series of switches is coupled to one of the one or more control wires.

4. The electrosurgical connection unit of claim 3, wherein at least one of the one or more activation switch units comprise at least two switches in series.

5. The electrosurgical connection unit of claim 1, wherein the one or more activation switch units comprises a first activation switch unit and a second activation switch unit.

6. The electrosurgical connection unit of claim 5, wherein when the input port is connected to the electrosurgical generator, activating the first activation switch unit causes a first activation signal to be transmitted to the electrosurgical generator which causes the electrosurgical generator to output a driving electrosurgical signal with a first waveform, and activating the second activation switch unit causes a second activation signal to be transmitted to the electrosurgical generator which causes the electrosurgical generator to output a driving electrosurgical signal with a second waveform.

7. The electrosurgical connection unit of claim 1, wherein the desired waveform is one waveform of a plurality of waveforms supported by the electrosurgical generator.

8. The electrosurgical connection unit of claim 1, wherein the input port is configured to receive a single cable over which the driving electrosurgical signal is received from the electrosurgical generator and the one or more activation signals are transmitted to the electrosurgical generator.

9. The electrosurgical connection unit of claim 1, wherein the output port is configured to receive a cable over which the driving electrosurgical signal is transmitted to the electrosurgical instrument.

10. The electrosurgical connection unit of claim 1, wherein the output port is further configured to receive a return electrosurgical signal from the electrosurgical instrument or a return electrode, and the input port is configured to output the return electrosurgical signal received on the output port.

11. The electrosurgical connection unit of claim 1, wherein the control unit is configured to activate an activation switch unit of the one or more activation switch units by outputting one or more signals that cause the activation switch unit of the one or more activation switch units to be activated.

12. The electrosurgical connection unit of claim 1, further comprising an isolation device that forms an isolation barrier between the one or more activation switch units and the control unit.

13. The electrosurgical connection unit of claim 1, further comprising one or more alternating current coupling circuits, the or each alternating current coupling circuit of the one or more alternating current coupling circuits being situated between the control unit and a respective one of the one or more activation switch units, wherein the or each alternating current coupling circuit of the one or more activation current coupling circuits is configured to receive a signal output by the control unit and generate a direct current filtered version of the signal.

14. The electrosurgical connection unit of claim 1, wherein the measurement unit is an impedance measurement device configured to measure an impedance across that activation switch unit of the one or more activation switch units.

15. The electrosurgical connection unit of claim 1, further comprising a capacitance emulation unit configured to present a predetermined capacitance to the electrosurgical generator when the electrosurgical generator is connected to the input port and activation of an activation switch unit of the one or more activation switch units causes an activation signal to be transmitted to the electrosurgical generator.

16. The electrosurgical connection unit of claim 1, wherein the control unit is configured to generate a token comprising information indicating a time at which the token was generated, and transmit the token to an external computing device, and the control signal is a modified version of the token that further comprises information indicating the desired waveform.

17. The electrosurgical connection unit of claim 16, wherein the control unit is configured to only activate an activation switch unit of the one or more activation switch units in response to receiving the modified version of the token when at the time the modified version of the token is received at the control unit an elapsed time since the token was generated is less than a threshold.

18. A surgical robot arm comprising the electrosurgical connection unit of claim 1.

19. The surgical robot arm of claim 18, wherein the electrosurgical connection unit is removably attached to the surgical robot arm.

20. A surgical robotic system comprising:
an electrosurgical generator;
an electrosurgical instrument;
a surgical robot arm comprising an electrosurgical connection unit, the electrosurgical connection unit comprising;
an input port connectable to the electrosurgical generator, wherein when the input port is connected to the electrosurgical generator, the input port is configured to:
output one or more activation signals to the electrosurgical generator which cause the electrosurgical generator to output a driving electrosurgical signal configured to drive the electrosurgical instrument, and
receive the driving electrosurgical signal output by the electrosurgical generator;
an output port connectable to the electrosurgical instrument, the output port configured to output the driving electrosurgical signal received on the input port;
one or more activation switch units, wherein activation of an activation switch unit of the one or more activation switch units causes an activation signal to be output from the input port that indicates to the electrosurgical generator that a desired waveform is to be used to generate the driving electrosurgical signal;
a control unit configured to selectively activate one of the one or more activation switch units in response to a control signal; and
a measurement unit configured to measure a parameter of an activation switch unit of the one or more activation switch units and output measurement information to the control unit, the measurement information enabling a determination to be made as whether that activation switch unit of the one or more activation switch units is operating as expected.

* * * * *